(12) United States Patent
Katayama et al.

(10) Patent No.: US 11,535,821 B2
(45) Date of Patent: Dec. 27, 2022

(54) CO-CULTURE DEVICE FOR ANAEROBIC BACTERIUM AND EPITHELIAL CELLS

(71) Applicant: Kyoto University, Kyoto (JP)

(72) Inventors: Takane Katayama, Kyoto (JP); Taiho Kambe, Kyoto (JP)

(73) Assignee: Kyoto University, Kyoto (JP)

( * ) Notice: Subject to any disclaimer, the term of this patent is extended or adjusted under 35 U.S.C. 154(b) by 134 days.

(21) Appl. No.: 16/344,562

(22) PCT Filed: Oct. 30, 2017

(86) PCT No.: PCT/JP2017/039206
§ 371 (c)(1),
(2) Date: Apr. 24, 2019

(87) PCT Pub. No.: WO2018/079793
PCT Pub. Date: May 3, 2018

(65) Prior Publication Data
US 2019/0382703 A1    Dec. 19, 2019

(30) Foreign Application Priority Data

Oct. 28, 2016 (JP) .............................. JP2016-211626

(51) Int. Cl.
*C12M 1/00* (2006.01)
*C12M 1/12* (2006.01)

(52) U.S. Cl.
CPC ............ *C12M 23/34* (2013.01); *C12M 25/02* (2013.01)

(58) Field of Classification Search
CPC ... C12M 23/34; C12M 25/02; C12N 2501/23; C12N 2501/39; C12N 2502/16
USPC ................... 435/303.2, 262, 294.1
See application file for complete search history.

(56) References Cited

U.S. PATENT DOCUMENTS 8,178,345 B2 *  5/2012  Bennett ................. C12M 23/34
                                              435/304.2
10,625,264 B2 *  4/2020  Hong .................... C12M 23/12
                         (Continued)

FOREIGN PATENT DOCUMENTS

JP    2005102657 A  *  4/2005  ............ C12M 23/24
JP    2014-506801 A     3/2014
                    (Continued)

OTHER PUBLICATIONS

JP2005102657A—Takaoki et al. Machine English Translation (Year: 2005).*
(Continued)

*Primary Examiner* — Michael L Hobbs
*Assistant Examiner* — Lenora A Abel
(74) *Attorney, Agent, or Firm* — Morgan, Lewis & Bockius LLP

(57) ABSTRACT

A culture system for co-culturing a first cell group consisting of one or more kinds of cells and a cell layer or tissue formed of a second cell group consisting of one or more kinds of cells different from the former cells comprising: a first culture tank for co-culturing under anaerobic conditions the first cell group consisting of one or more kinds of cells and the cell layer or tissue formed of the second cell group consisting of one or more kinds of cells; a second culture tank for pooling a liquid culture medium of aerobic conditions; one or more substance-exchange structures that are disposed so as to connect the first culture tank to the second culture tank; and the aforesaid cell layer or tissue that is disposed so as to cover the surface on the first culture tank side of the substance-exchange structure(s).

5 Claims, 17 Drawing Sheets

(56) References Cited

U.S. PATENT DOCUMENTS

| | | | |
|---|---|---|---|
| 2014/0038279 A1* | 2/2014 | Ingber | C12M 23/38 |
| | | | 435/297.2 |
| 2015/0072413 A1* | 3/2015 | Zenhausern | C12M 35/08 |
| | | | 435/347 |
| 2015/0147806 A1* | 5/2015 | Char | C12N 5/0693 |
| | | | 435/347 |
| 2016/0002585 A1 | 1/2016 | Reid et al. | |
| 2017/0101628 A1 | 4/2017 | Ingber et al. | |
| 2017/0342365 A1 | 11/2017 | Nozaki et al. | |

FOREIGN PATENT DOCUMENTS

| | | | |
|---|---|---|---|
| WO | 2012/118799 A2 | 9/2012 | |
| WO | WO-2014120702 A1 * | 8/2014 | C12M 23/12 |
| WO | 2016/157322 A1 | 10/2016 | |

OTHER PUBLICATIONS

Huh et al., "Microengineered physiological biomimicry: Organs-on-Chips," Lab Chip, 12: 2156-2164 (2012).
Extended European Search Report issued in corresponding European Patent Application No. 17866038.7 dated Oct. 13, 2020.
Ulluwishewa et al., "Live Faecalibacterium prausnitzii in an apical anaerobic model of the intestinal epithelial barrier," Cellular Microbiology, 17 (2): 226-240 (2015).
Office Action issued in Chinese Patent Application No. 201780077207.0 dated Jan. 27, 2022.

* cited by examiner

[FIG. 1]
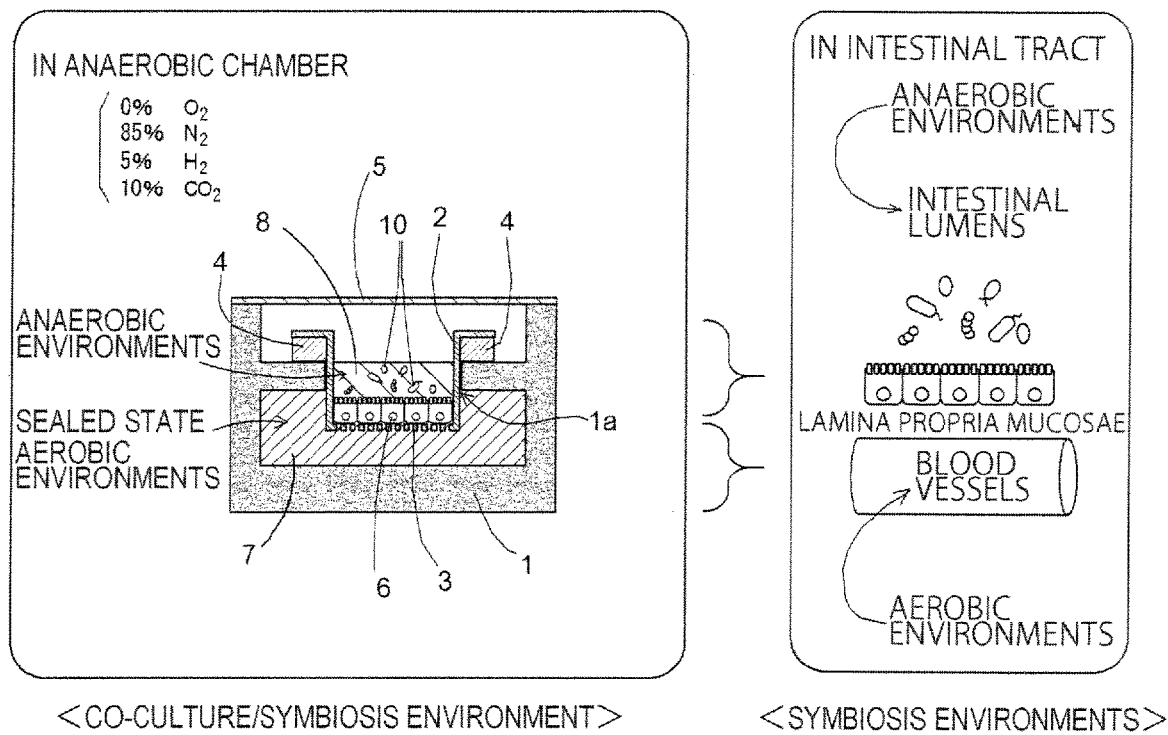
[FIG. 2]
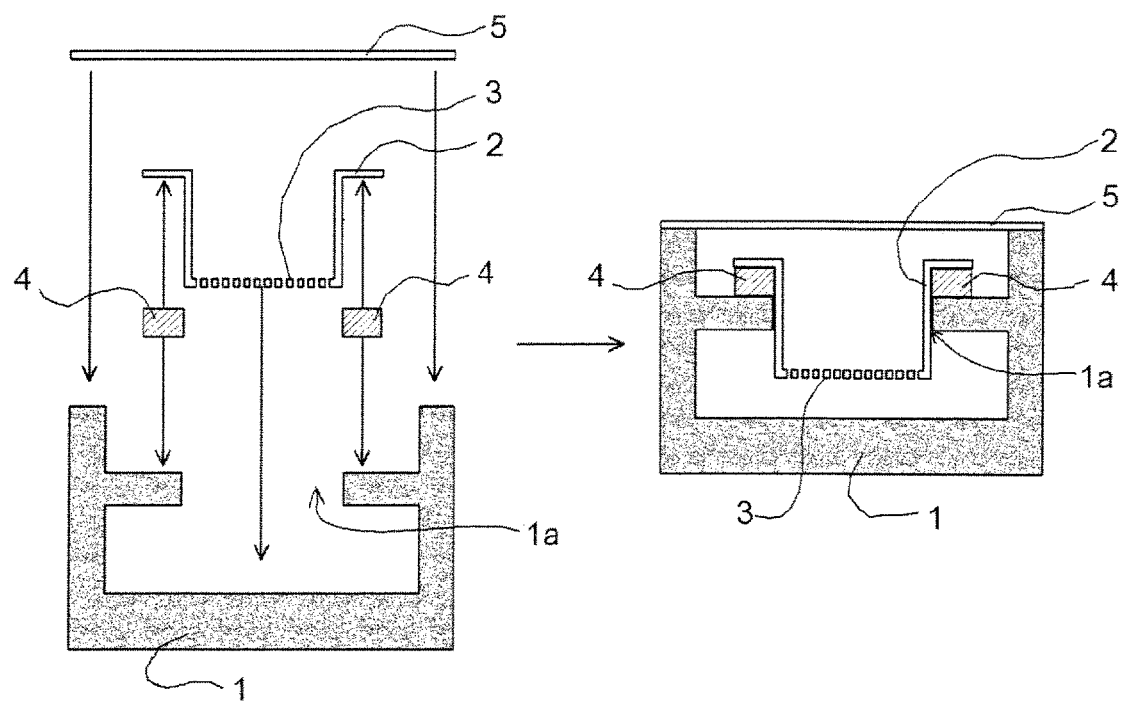

[FIG. 3]
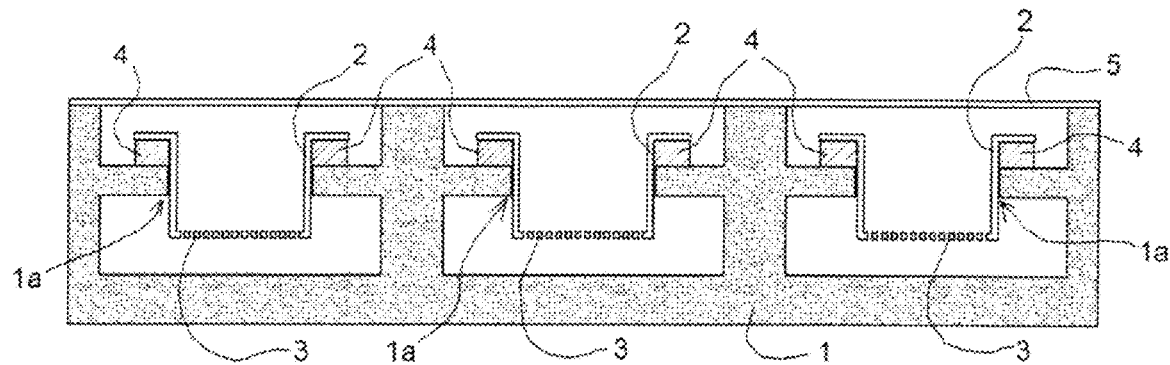
[FIG. 4]
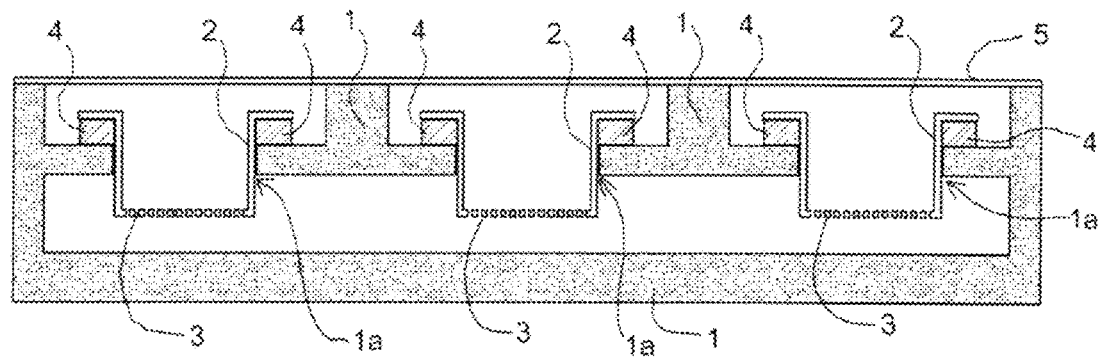
[FIG. 5]
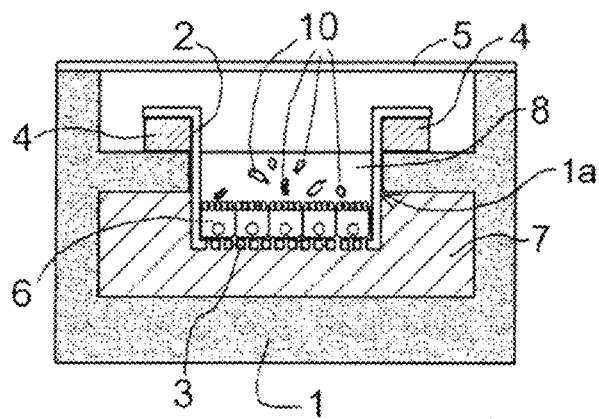

[FIG. 6]
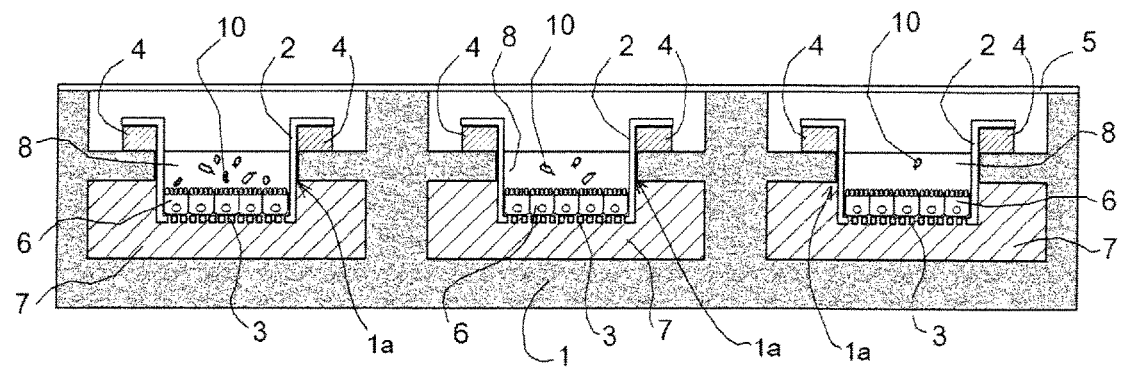
[FIG. 7]
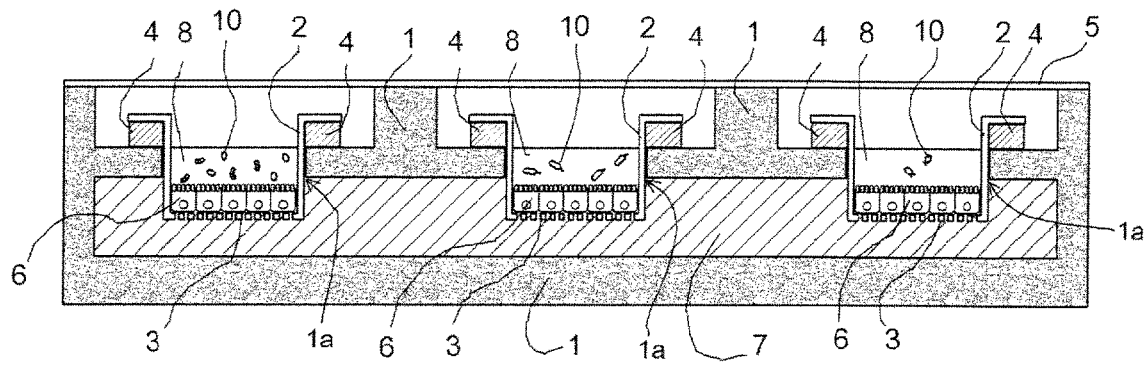
[FIG. 8]
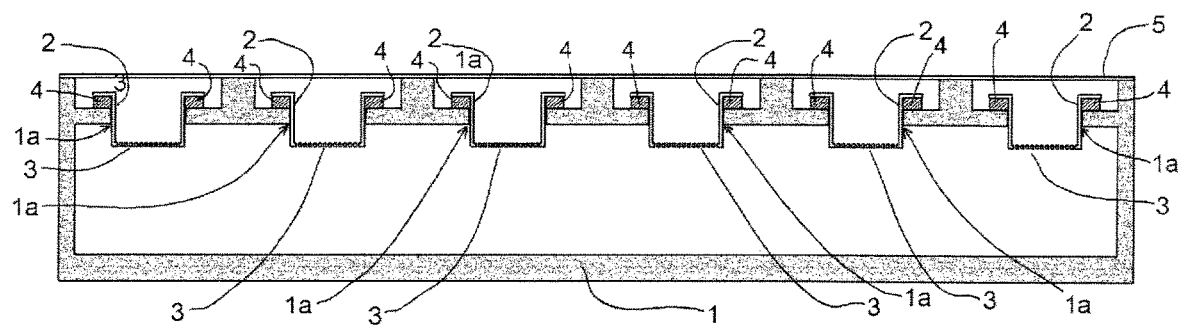

[FIG. 9]
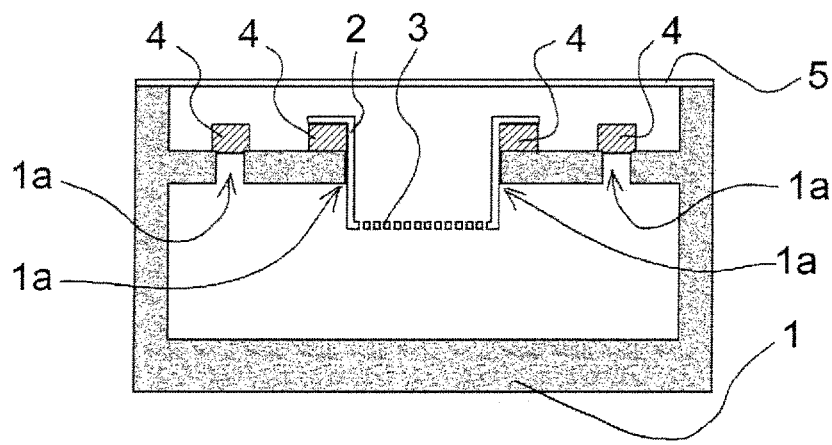
[FIG. 10]
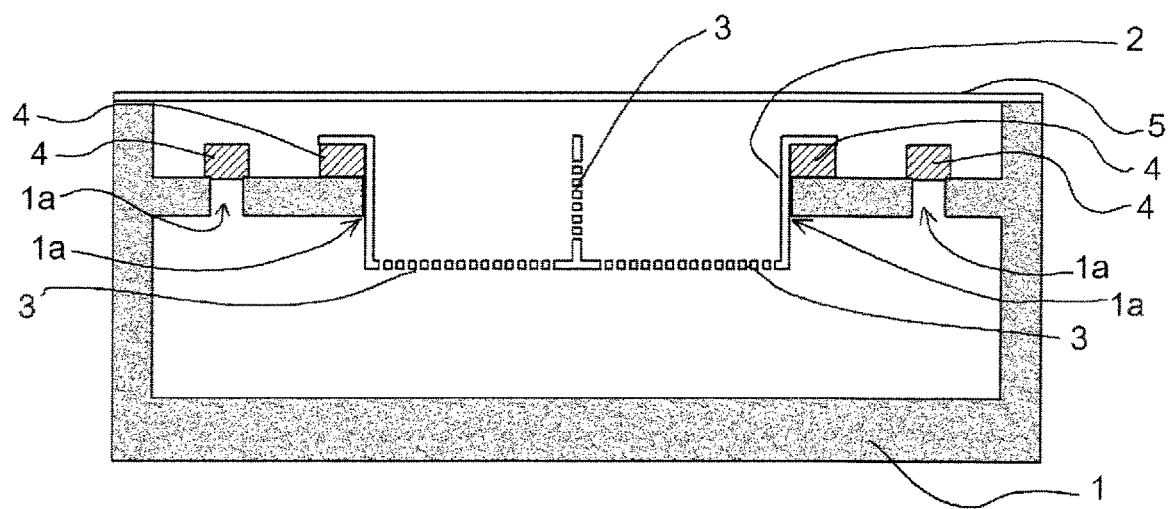

[FIG. 11]
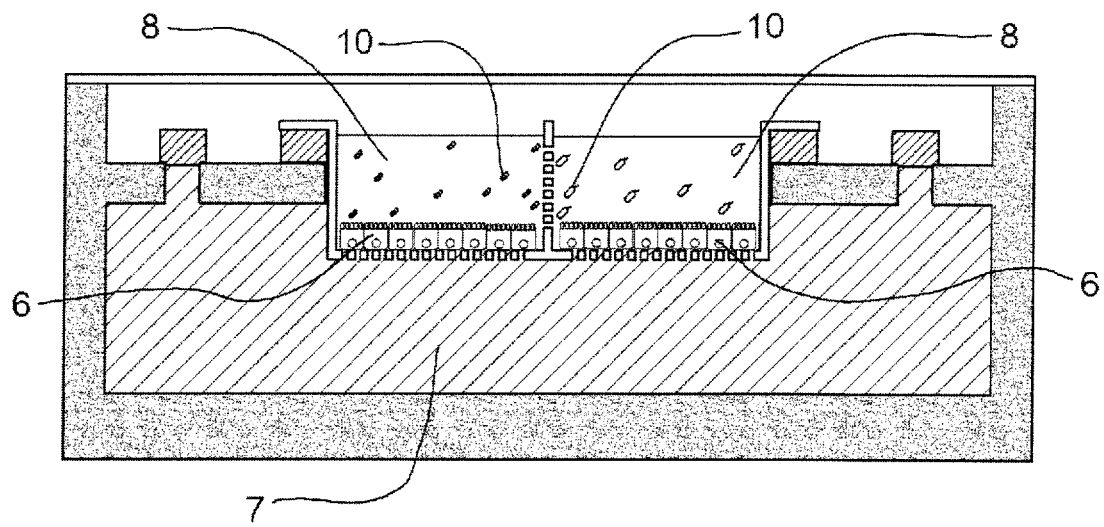
[FIG. 12]
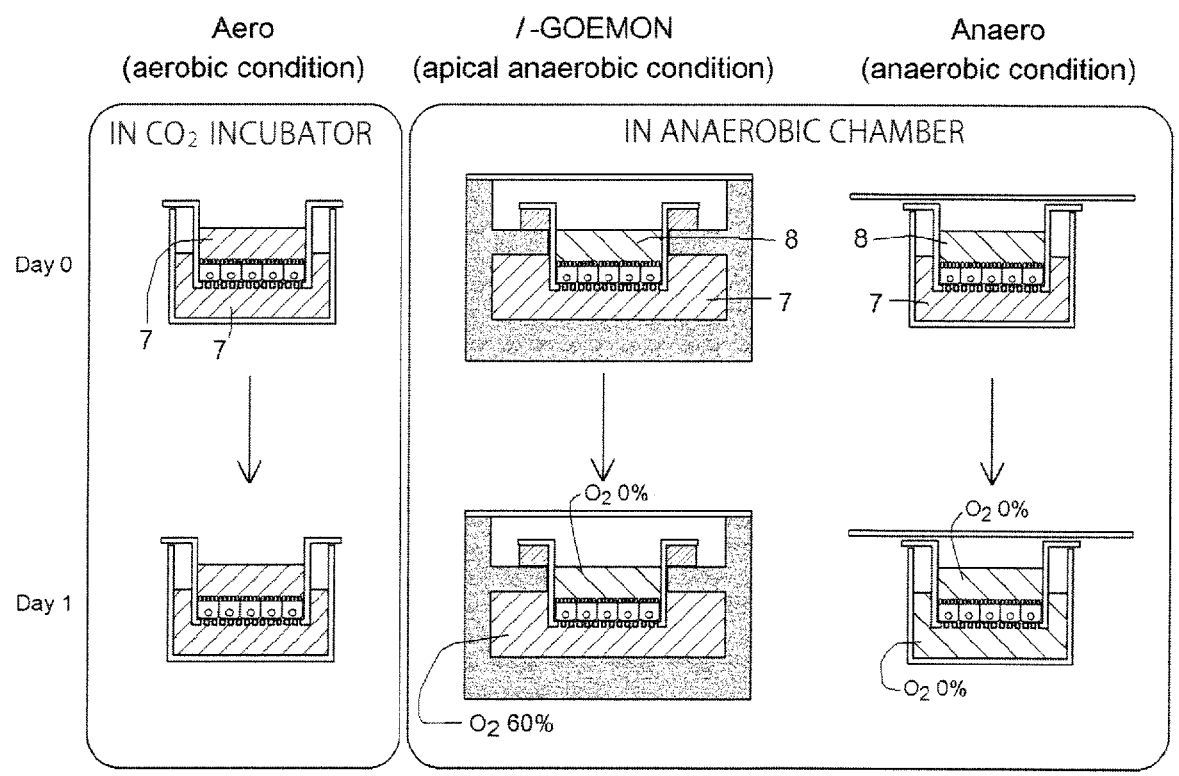

[FIG. 13]
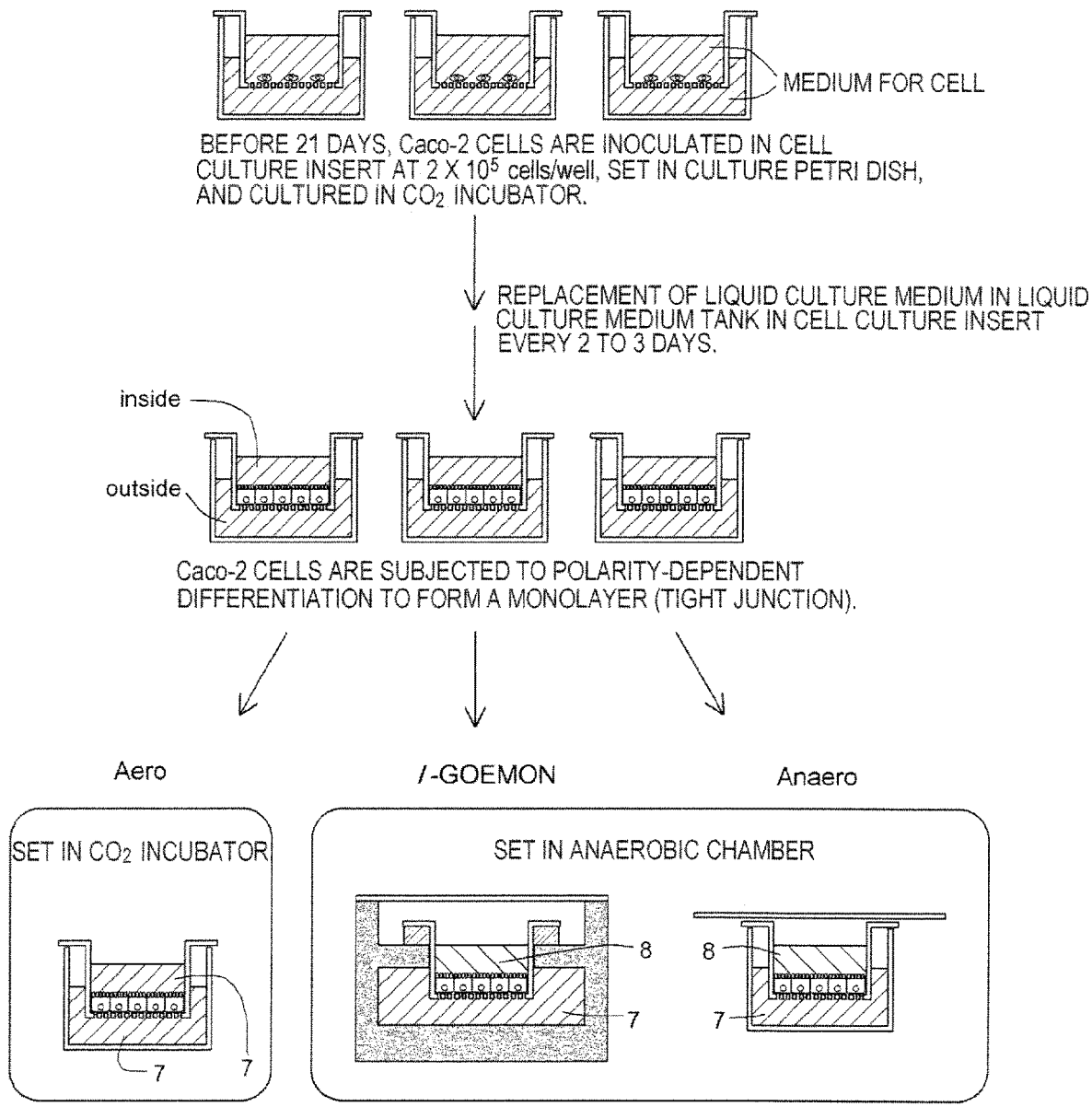

[FIG. 14]
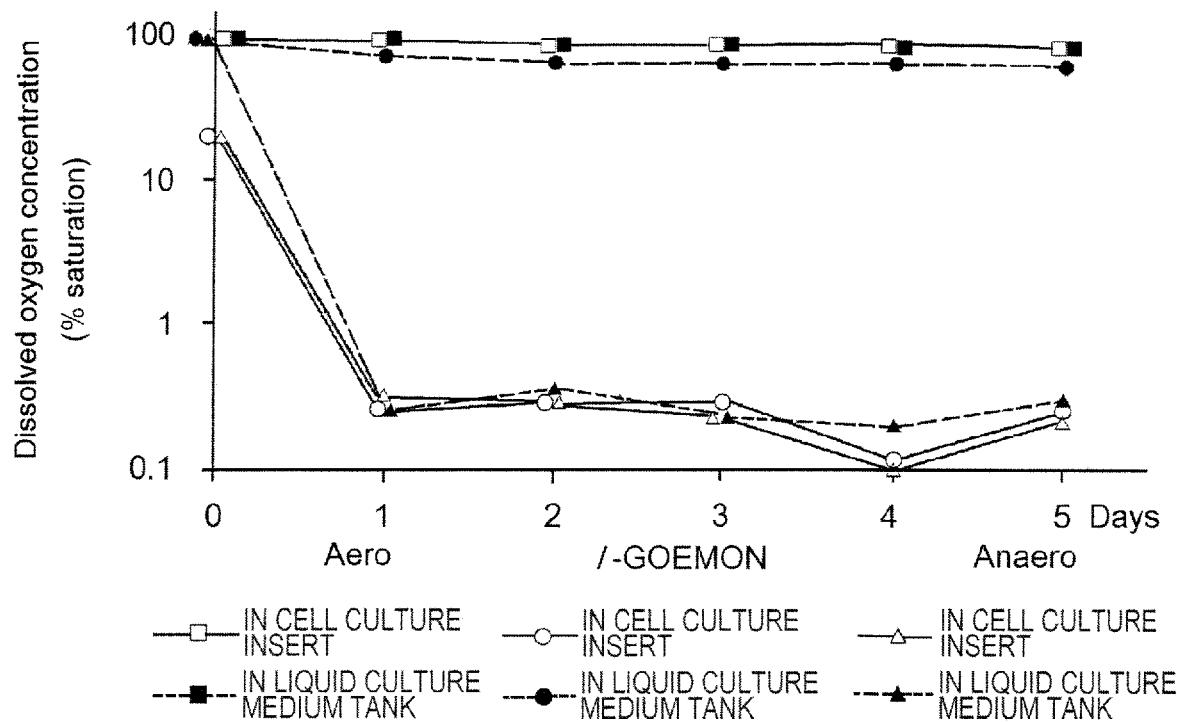
[FIG. 15]
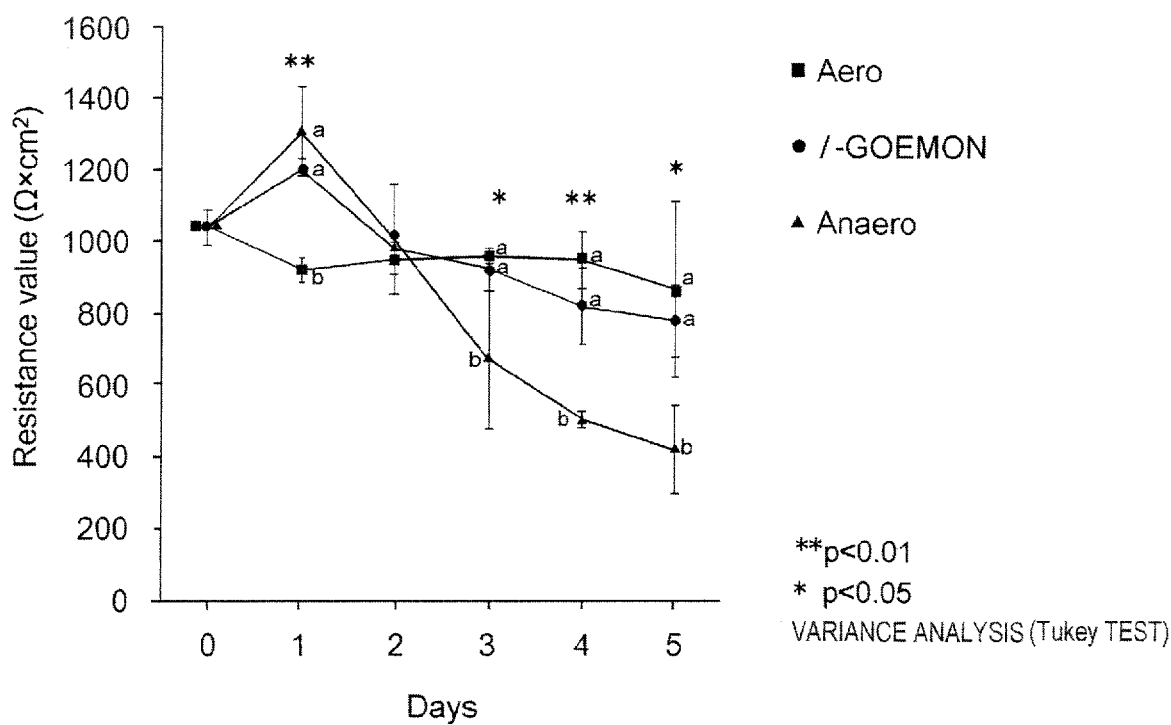

[FIG. 16]
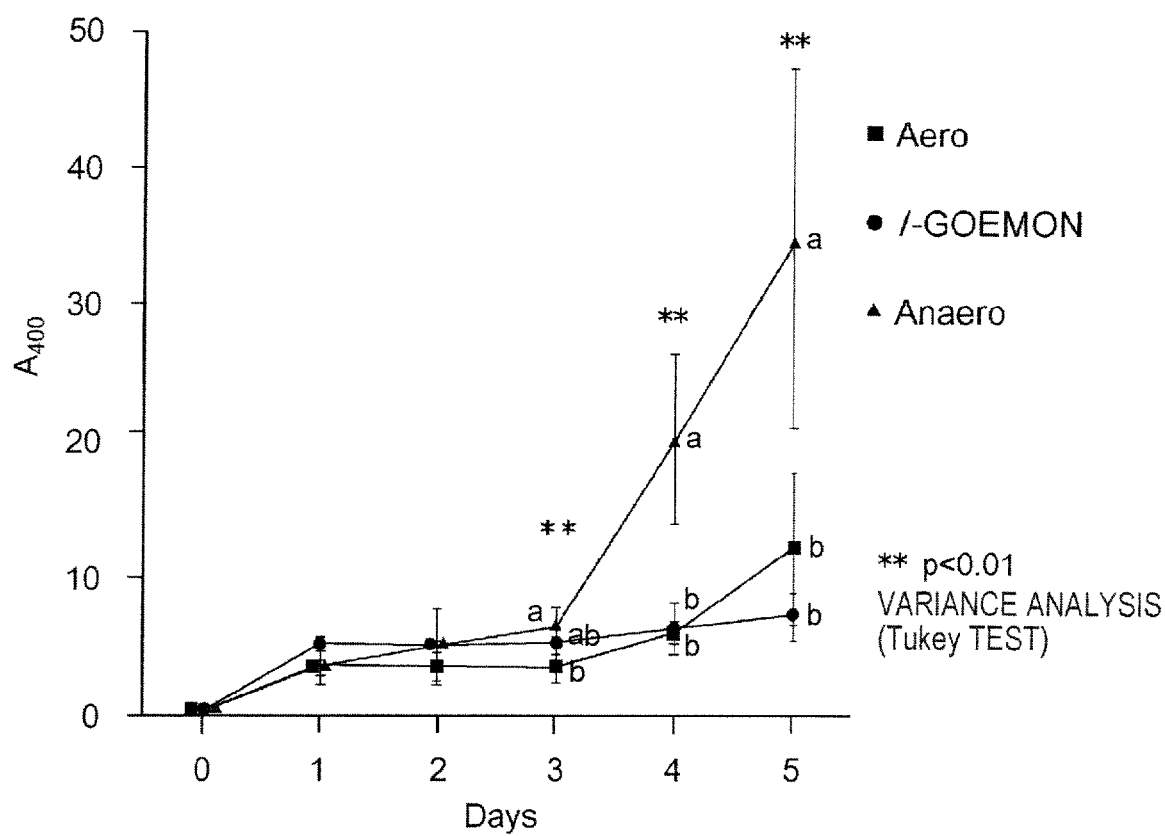

[FIG. 17]
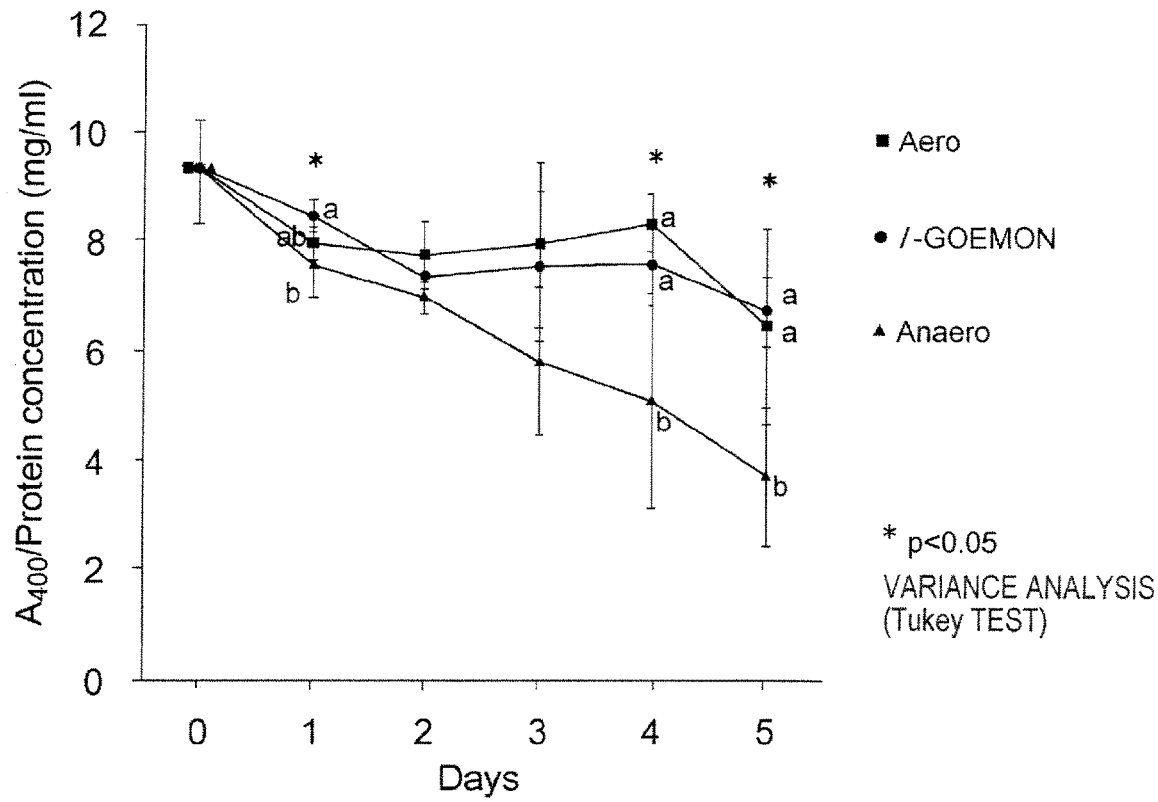
[FIG. 18]
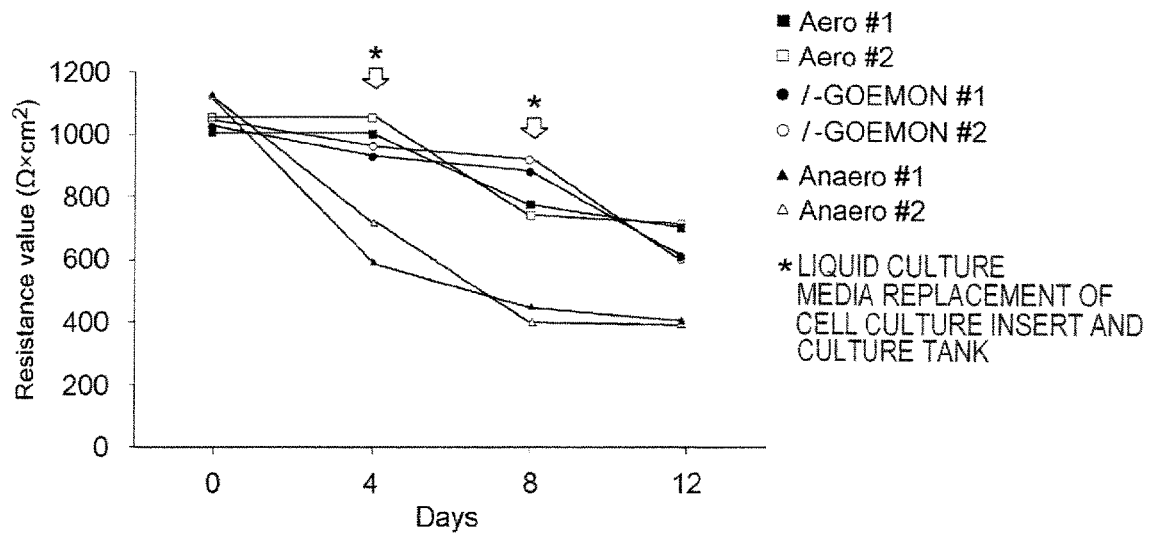

[FIG. 19]
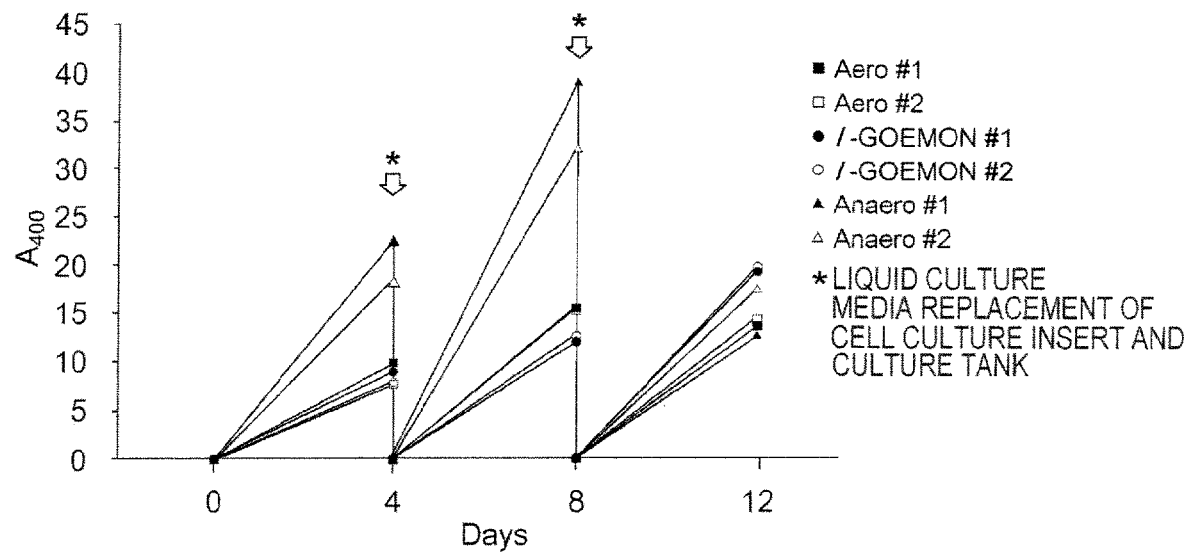
[FIG. 20]
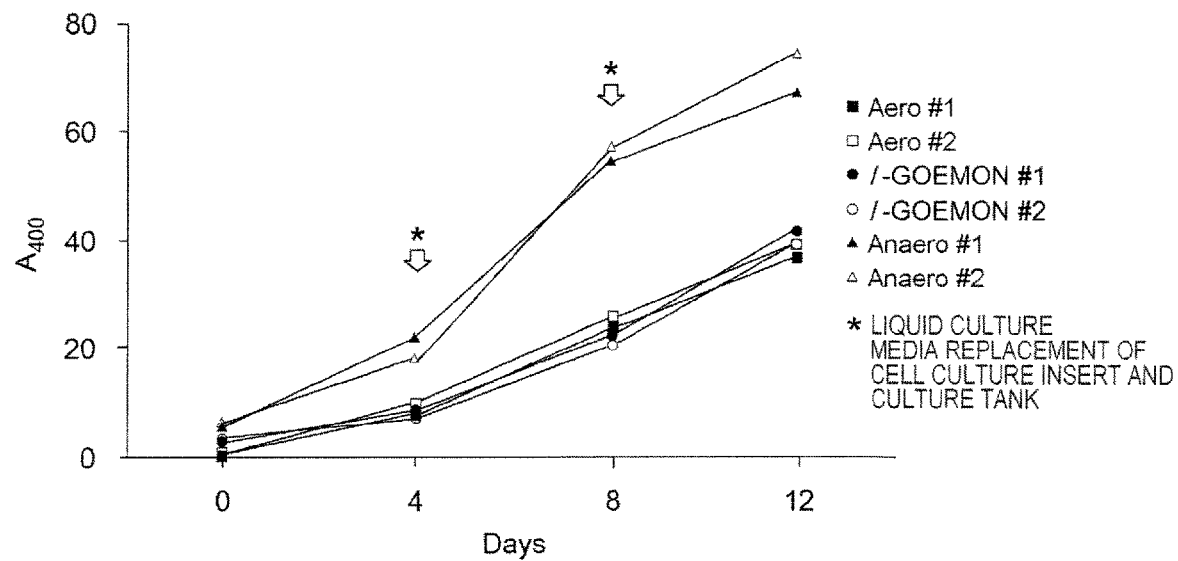

[FIG. 22]
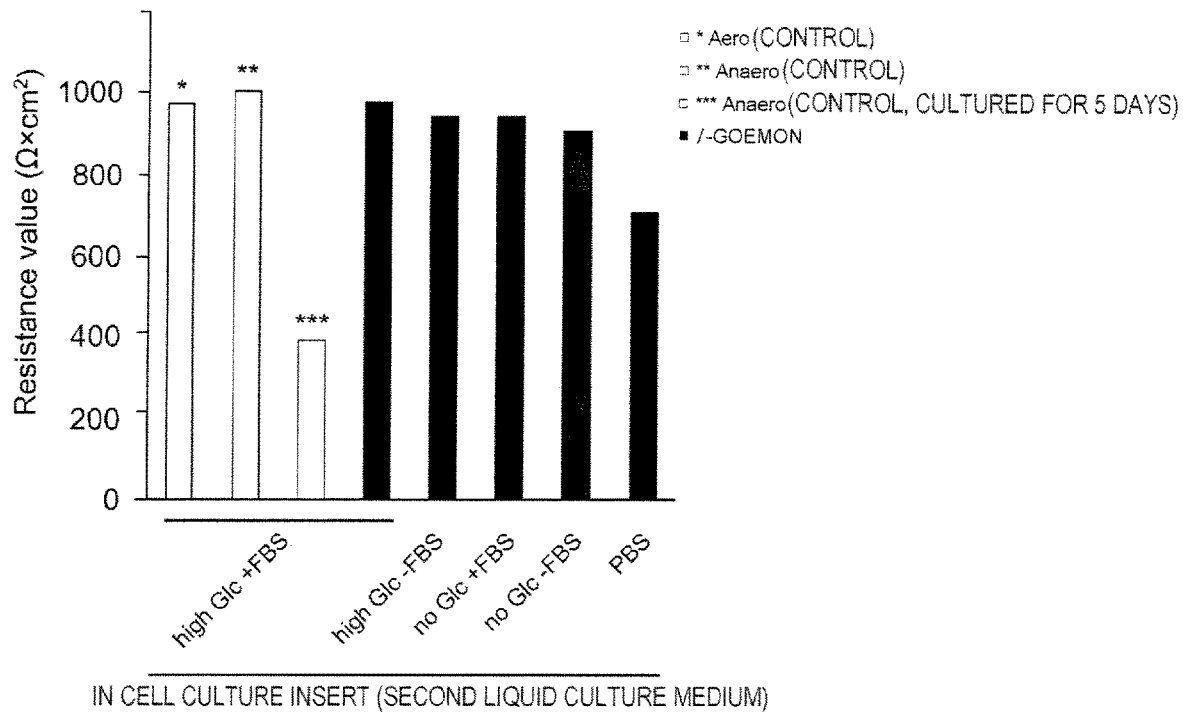
[FIG. 23]
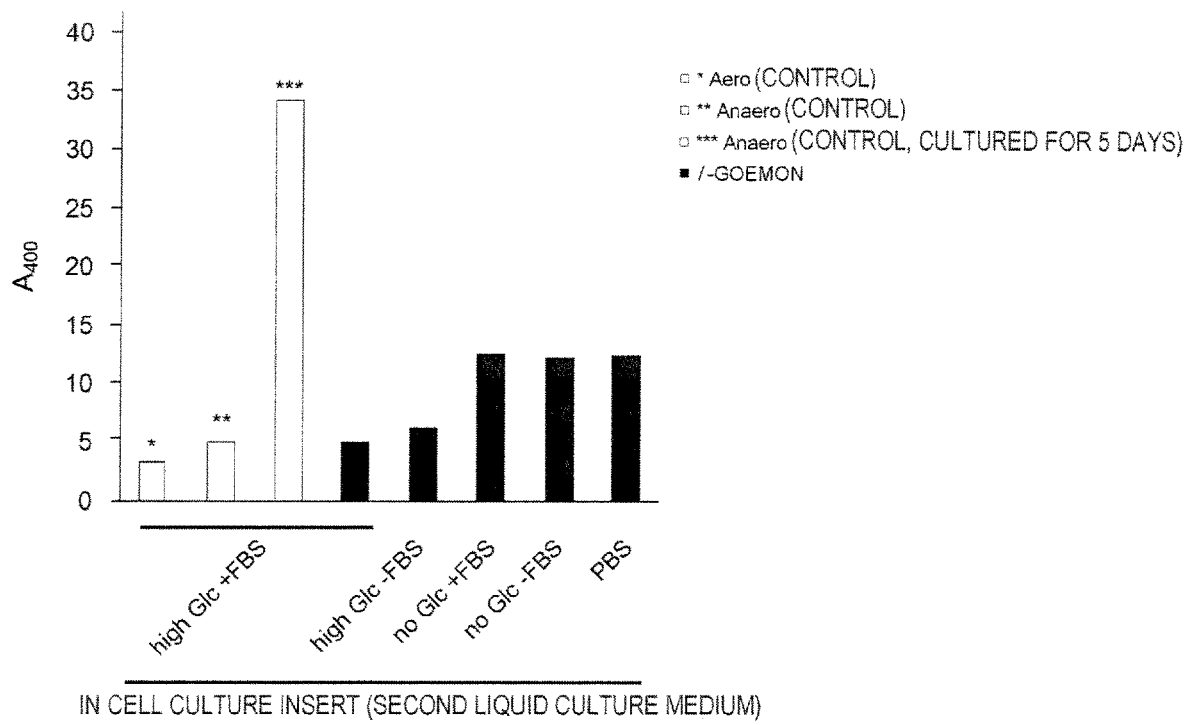

[FIG. 25]
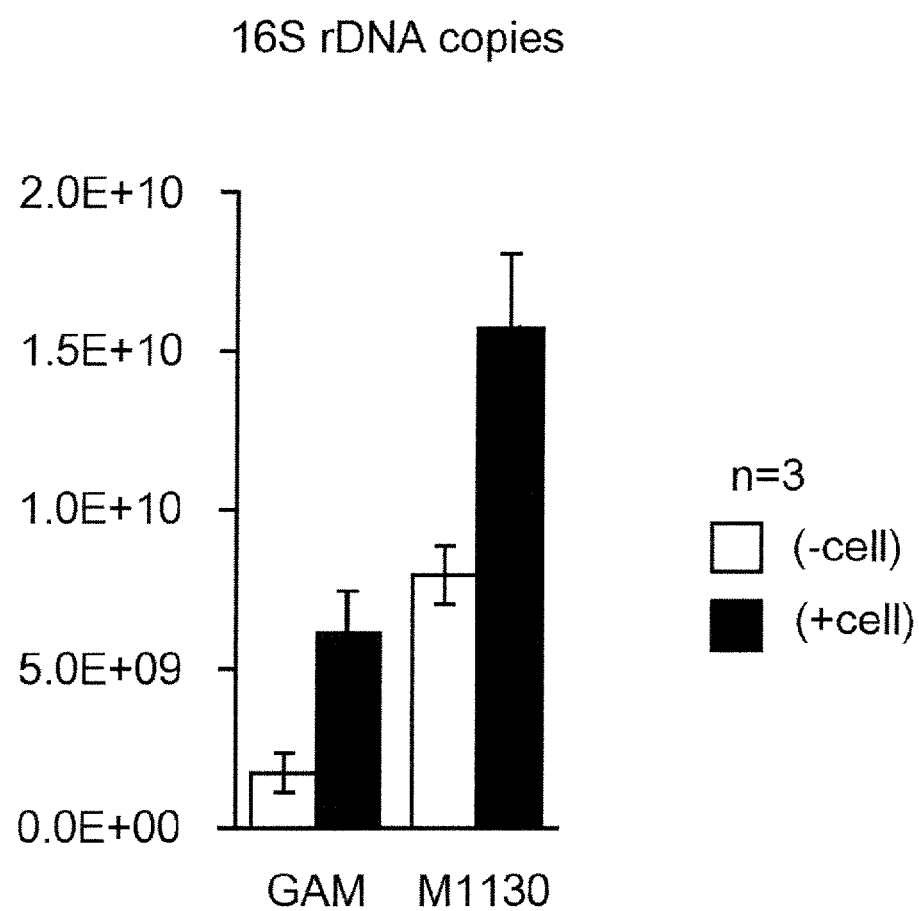

[FIG. 26]
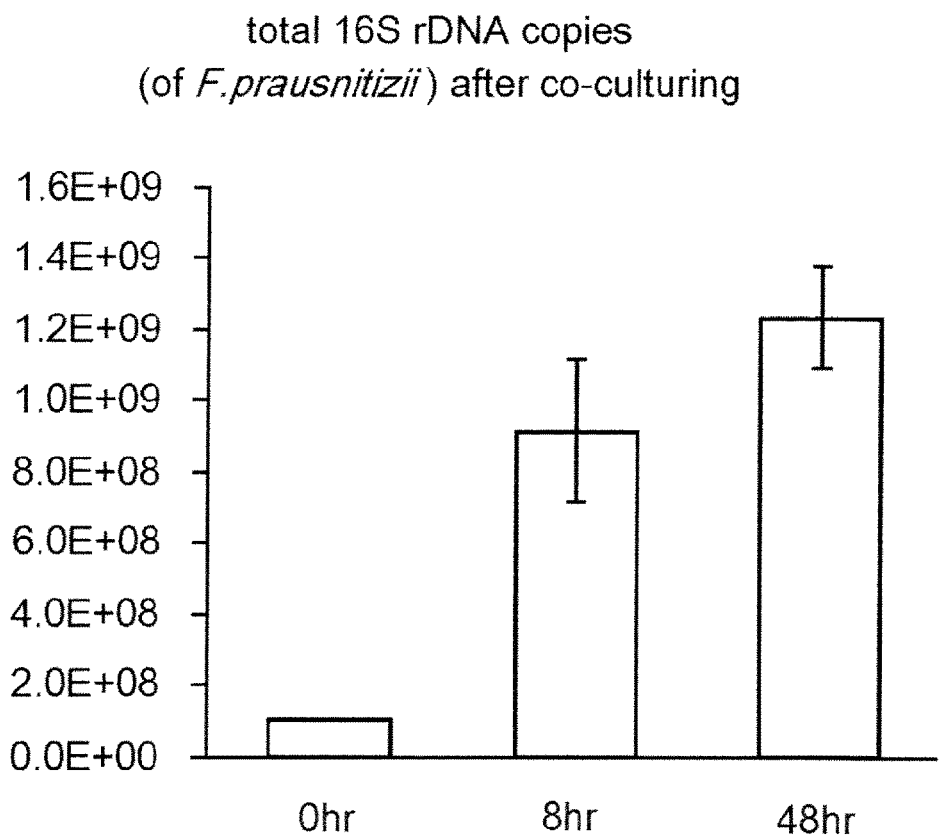
[FIG. 27]
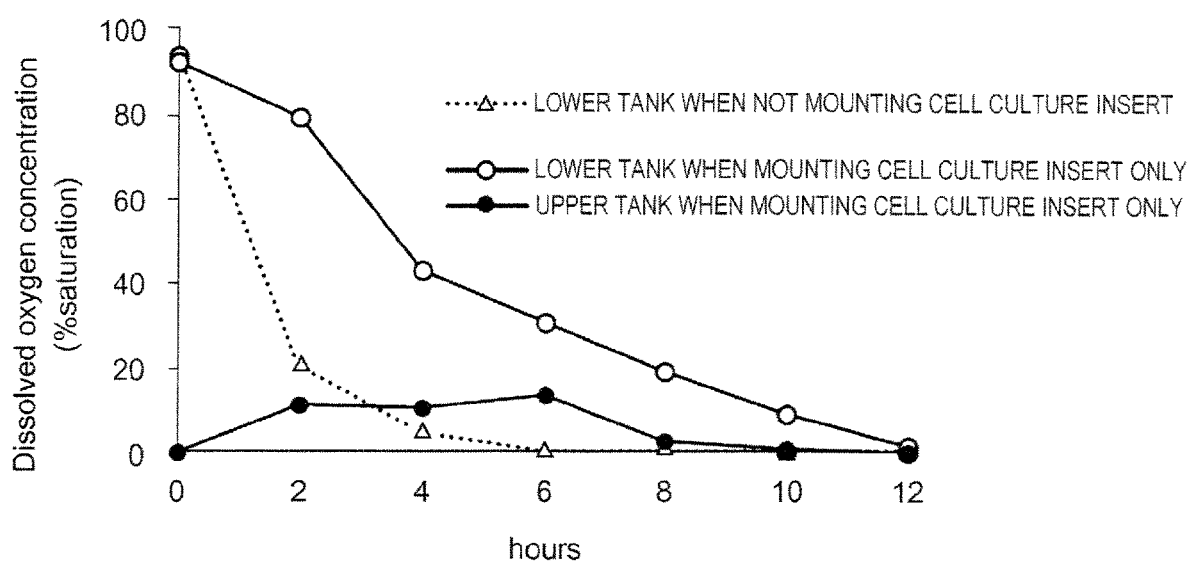

[FIG. 28]
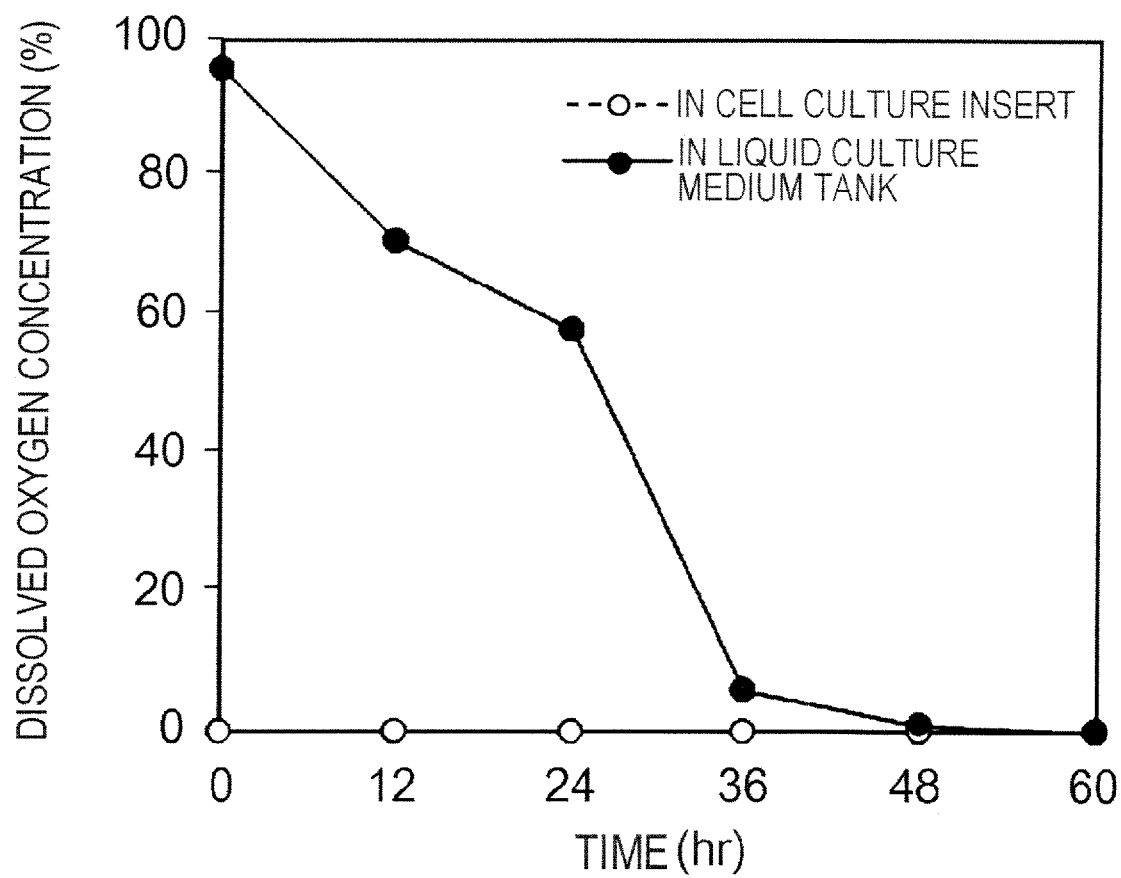

[FIG. 29]
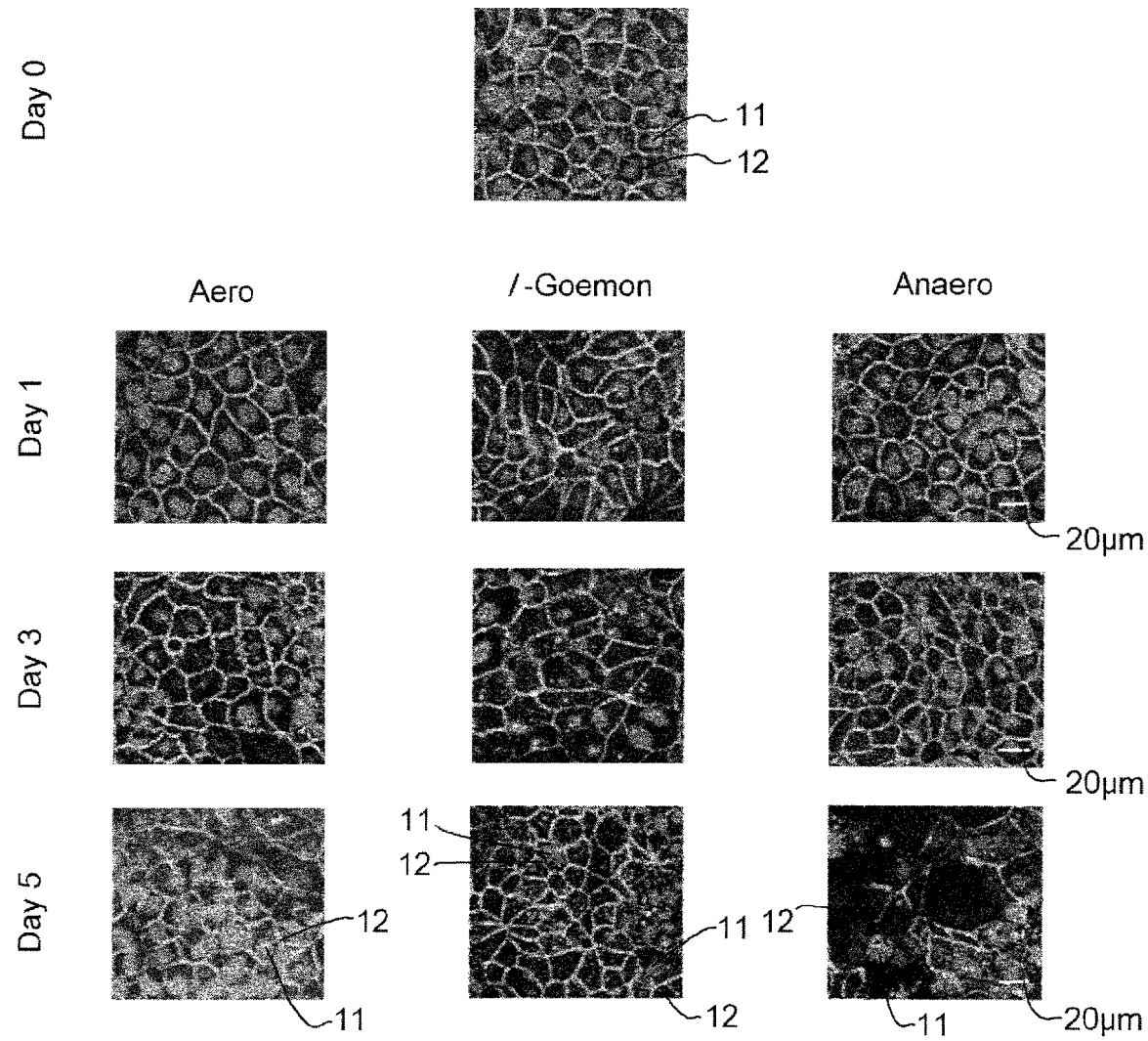
11: nucleus (DAPI)
12: tight junction (anti Claudin-2 antibody)

CO-CULTURE DEVICE FOR ANAEROBIC BACTERIUM AND EPITHELIAL CELLS

TECHNICAL FIELD

The present disclosure relates to a co-culture device for co-culturing a bacterium (e.g. an anaerobic bacterium) with epithelial cells, and a co-culture method for a bacterium (e.g. an anaerobic bacterium) with epithelial cells using the device, and particularly, to a culture device for co-culturing a bacterium (e.g. an anaerobic bacterium) with epithelial cells in a state of being placed in an anaerobic chamber, and a co-culture method using the device.

BACKGROUND ART

Enteric bacteria are a generic term for indigenous and symbiotic bacteria in intestines of humans and animals. Enteric bacteria occur in high abundance and in the wide variety of species. More than 100 billion enteric bacteria would occur per gram of human gastrointestinal contents (feces), including at least approximately 100 different species with unidentified varieties. Most of enteric bacteria are recognized as anaerobes since they are in anaerobic environments of intestines.

Those enteric bacteria in human or other animal intestines would take up various substances included in their ingested foods; and metabolize them into products. This assists the hosts' digestive system process. In addition, enteric bacteria would inhabit intestines and establish stable gastrointestinal microbiota to prevent growth of foreign pathogens in the hosts' intestines and their resultant diseases. To the contrary, in some cases, enteric bacteria may produce as their metabolites, substances harmful or potentially life-threatening to their human or other animal hosts, including e.g. toxic substances, carcinogens and the like. Exposure to the intestines of human or other animal hosts, intestinal absorption, blood-mediated transportation and the resultant systemic delivery, of those substances would cause impaired physical conditions of the hosts, in faun of various disorders and diseases.

As stated above, enteric bacteria inhabit their hosts' intestines; and they form gastrointestinal microbiota. They occur in high abundance and in the wide variety of species. Such enteric bacteria and gastrointestinal microbiota influence the health of human or other animal hosts since, in certain cases, they maintain physical condition of the hosts and in other cases, they may be capable of causing diseases.

Populations and types of enteric bacteria as well as compositions of gastrointestinal microbiota can vary widely among different individuals. Even within an individual, ratios and types of enteric bacteria can vary over time through changes in external factors such as diet and lifestyle, and in internal factors such as physical conditions of the hosts. Therefore, physical conditions of human or other animal hosts can vary over time to reflect compositions of gastrointestinal microbiota in the hosts.

Recently, crucial roles of enteric bacteria and gastrointestinal microbiota have been at the center of attention for their influences on, and relationship to, human or other animal hosts' physical conditions. Further, this has enhanced opportunities for elucidation of contributing factors to their hosts' physical conditions; and for established applications of enteric bacteria and gastrointestinal microbiota to health promotion, treatment and disease prevention for the hosts. Then, in order to grasp whole picture of gastrointestinal microbiota, considerable efforts have been made to collect, to isolate, to culture, and to identify types and characteristics of enteric bacteria from intestines of humans or animals. Some enteric bacteria culturable (cultivable) under aerobic conditions have been isolated, identified, and biologically characterized in vitro. In addition, some aerobic enteric bacteria have been co-cultured with intestinal epithelial cells to elucidate the cross-talk between bacteria and epithelial cells. However, a large proportion of enteric bacteria are obligate anaerobic; and the majority are uncultivable. Consequentially, a limited or small number of enteric bacteria have been identified and characterized. Thus, accurate interpretation of enteric bacteria remains a considerable challenge, especially, concerning what external or internal factors effect change in type and ratio of enteric bacteria.

Several cultivation methods have been developed in considering that most enteric bacteria inhabit strictly anaerobic intestinal conditions. Specifically, provided were the methods of culturing enteric bacteria in liquid culture media contained in culture dishes placed in anoxic chambers. Those methods may be applied only to some enteric bacteria cultivable in liquid culture media. Further, those methods would require liquid culture medium compositions optimized individually for bacterium species. Some types of enteric bacteria among gastrointestinal microbiota had conditions optimized for their proliferation when the methods were used, while other types among the microbiota were uncultured and not proliferated under the aforementioned conditions. Therefore, the technical problems still remain in those methods.

Enteric bacteria would inhabit intestines in contact with epithelial cells of intestinal tracts. In light of the fact, systems were attempted for cocultivation of enteric bacteria with epithelial cells of intestinal tracts. The systems include monolayers of intestinal epithelial cells or equivalents so as to maintain enteric anaerobic bacteria in coexistence of the intestinal epithelial cells despite culturing the bacteria in liquid culture media; or in some cases, the systems include monolayers of intestinal epithelial cells or equivalents, prepared on filters for cell culture systems harboring cell culture inserts. However, the monolayers of the epithelial cells or equivalents got destroyed under anoxic environments, specifically the tight junctions between the cells got disrupted in one day, the cells were dead within 48 hours, the monolayers were detached (Patent Literature 1). Therefore, the systems have not accomplished cocultivation of enteric bacteria with epithelial cells of intestinal tracts.

Further, a co-culture system for enteric bacteria and intestinal epithelial cells has been proposed. The system includes vacuum chambers, a microchannel and a porous membrane having one layer of intestinal epithelial cells attached thereto. The membrane divides the microchannel into two culture channels such that one cell culture channel is located directly above the other cell culture channel. The two culture channels are individually connected to different fluid sources; and the two sources hold and supply different fluids to the channels. The vacuum chambers are positioned on either side of the microchannel to repeatedly stretch and relax the porous membrane (Patent Literature 1).

CITATION LIST

Patent Literature

Patent Literature 1: JP-A-2014-506801

SUMMARY OF INVENTION

Technical Problem

The problem to be solved by the present disclosure is to provide a new measure of a low-cost co-culture system of a bacterium, e.g. an anaerobic bacterium with epithelial cells; as well as a culture method using the co-culture system. The system is configured to easily, simply, and efficiently proliferate a bacterium, e.g. an obligate anaerobic uncultivable bacterium or the like while maintaining a symbiotic relationship with the epithelial cells or equivalents. The system does not require special culture environments, e.g. environments established by repeatedly stretching and relaxing monolayer membranes while supplying a liquid culture medium to the membranes. Further, the problem to be solved by the present disclosure is also to isolate, culture, identify and characterize bacteria as yet unidentified, especially anaerobic bacteria, by using the culture system and the culture method.

In addition, the problem to be solved by the present disclosure is to provide the above-stated new co-culture system of bacterium, e.g. an anaerobic bacterium, with epithelial cells as well as the culture method of using the system, as version thereof further including components for limiting dilution of bacteria, multiwell culture, general-purpose robot-based automation of passage culture.

Further, the problem to be solved by the present disclosure is to provide measure capable of substantially realizing a mixed culture of bacteria (e.g. obligate anaerobic uncultivable bacteria), by compartmentalizing the culture space. Each of the compartments has one of the isolated bacteria while maintaining a symbiotic relationship with epithelial cells or equivalents.

In addition, an additional problem to be solved by the present disclosure is to explain a symbiosis mechanism of a bacterium (e.g. an anaerobic bacterium) with epithelial cells; to clarify relationships between external or internal factors and changes in types and ratios of bacteria; to identify factors contributing to or adversely affecting health, involved in bacteria, bacterial flora, and metabolites thereof; to take advantage of such factors so as to establish health promotion, treatment and disease prevention of humans and animals.

Solutions to Problems

First measure of the present disclosure for solving the above problems is a culture system for co-culturing a first cell group consisting of one or more kinds of cells and a cell layer or tissue formed of a second cell group consisting of one or more kinds of cells different from the former cells; and the culture system includes: a first culture tank for co-culturing under anaerobic conditions the first cell group and the cell layer or tissue formed of the second cell group; a second culture tank for pooling a liquid culture medium under aerobic conditions; and one or more substance-exchange structures that are disposed so as to connect the first culture tank to the second culture tank and that are configured to maintain the cell layer or tissue so as to cover a surface at a side of the first culture tank.

Second measure of the present disclosure for solving the above problems is a culture system described in the first measure of the present disclosure, in which openings are closed between the second culture tank and the first culture tank so that an inside of the second culture tank is closed except for the substance-exchange structure; and a gas-impermeable sealing agent is provided at a connection part between the first culture tank and the second culture tank.

Third measure of the present disclosure for solving the above problems is a culture system described in the first measure or the second measure of the present disclosure in which the second culture tank includes a gas-permeable moisturizing member for sealing openings thereon to the outside so that the second culture tank has no part therein opened to the outside with openings sealed by the moisturizing member.

Fourth measure of the present disclosure for solving the above problems is a culture system described in any one of the first through the third measures of the present disclosure, in which the first culture tank includes a plurality of partial structures therein and substance-exchange structures other than the substance-exchange structure, each of the partial structures functions as a culture tank, each of the partial structures is individually interconnected by one of the other substance-exchange structures, and each of the plurality of partial structures is connected to the second culture tank.

Fifth measure of the present disclosure for solving the above problems is a culture system described in any one of the first through the fourth measures of the present disclosure in which the culture system is configured to be placed in an anaerobic chamber in use.

Sixth measure of the present disclosure for solving the above problems is a culture system for co-culturing a bacterium with a cell layer formed of epithelial cells, and the culture system includes a first culture tank configured to be used under anaerobic conditions; a second culture tank; and a gas-impermeable sealing agent. Further, the first culture tank has one or more substance-exchange structures in a bottom thereof so as to allow the cell layer to cover each top surface of the substance-exchange structures. The second culture tank is a tank for pooling a liquid culture medium of aerobic conditions, and has an opening for receiving the first culture tank so that the substance-exchange structure in the bottom of the first culture tank is immersed in the liquid culture medium of aerobic conditions pooled in the second culture tank.

Further, openings are closed between the second culture tank and the first culture tank so that an inside of the second culture tank is closed except for the substance-exchange structure. Gas-impermeable sealing agent is provided at a connection part between the first culture tank and the second culture tank; and the second culture tank includes a gas-permeable moisturizing member for sealing openings thereon to the outside so that the second culture tank has no part therein opened to the outside with openings sealed by the moisturizing member.

Aspects of a kit, a device, a culture method and the like will become apparent to those skilled in the art upon consideration of the embodiments described as a culture system in the present disclosure; and those other aspects also fall within the scope of the disclosure.

Advantageous Effects of Invention

Merely performing a simple operation of placing the culture device of the present disclosure in an anaerobic chamber allows for maintenance of epithelial cell layers in a preferable state under anaerobic conditions; for implementation of co-culture of a bacterium (e.g. an anaerobic bacterium) with the epithelial cells; and further for efficient proliferation of the bacterium (e.g. anaerobic bacterium) or the like. The simple operation is conducted without a special device for preparing a culture environment, which imitates the intestinal environment, such as a solution circulation mechanism and a stretching and relaxing mechanism. In this instance, the solution circulation mechanism circulates a solution of an intestinal epithelial cell culture surface during the culture to realize an environment having a flow rate, which has been required in the conventional system reproducing a co-culture or symbiotic environment. In addition, the stretching and relaxing mechanism manipulates a pressure applied to a membrane so as to stretch and relax the membrane, in which a layer of intestinal epithelial cells are hold for co-culture. Furthermore, those allow for coculturing under anaerobic conditions, epithelial cells and bacterial flora collected from a biological object so as to proliferate and isolate, uncultivable bacteria. The conventional technology had not reached them.

In addition, the culture device and the culture method using the culture device of the present disclosure are provided for proliferating a bacterium (e.g. an anaerobic bacterium) in the cell culture insert. This allows users to simply and easily collect a bacterium (e.g. an anaerobic bacterium) proliferated in the coculture environment by inserting a pipettor and the like from the upper portion of the device into the cell culture insert. It has remarkably enhanced operating efficiency, and further making it easier to perform limiting dilution and isolation of a bacterium (e.g. an anaerobic bacterium) cultured in a mixed state. In addition, the culture device of the present disclosure also allow for multi-wells format, high-throughput operation and automation in combination with a conventional system using a multi-pipettor, a dispenser, and a dispensing robot. Further, they may make it easier to conduct large-scale limiting dilution of bacteria, e.g. anaerobic bacteria cocultured, and isolate the bacteria more easily and quickly.

Further, the culture device of the present disclosure and the culture method using the culture device allow for establishment of a culture system to easily reproduce intravital environment conditions. Specifically, the culture tank of the device has openings formed therein, and each of the openings receives a cell culture insert so that the insert is immersed in a first liquid culture medium. Each of the cell culture inserts has a monolayer of epithelial cells on its bottom of porous membrane structure. The above configuration of the culture device also allows for maintenance of monolayers of the epithelial cells in favorable conditions. In addition, the cell culture insert with its bottom of porous membrane structure, further includes a plurality of compartments and partition walls of porous membrane structure; and the compartments are separated from one another by the walls. The compartments allow for parallel co-cultures of different bacteria under anaerobic conditions. Each of the bacteria is allocated in one of compartments, and subjected to co-culture with monolayer of the epithelial cells. Then, each compartment includes a different type of bacteria. This may eventually provide a culture system to establish a mixed co-culture of different bacteria.

In addition, the culture device of the present disclosure has a structure to facilitate user-friendly operations to change a first liquid culture medium and a second liquid culture medium; and to collect epithelial cells or bacteria during culturing in order to investigate a state of the cells or bacteria. This allows for modification of one of the liquid culture media interpedently from each other to facilitate studies of various factors (e.g., factors necessary for maintenance or proliferation of a layer of epithelial cells on a porous membrane in a cell culture insert or a bacterium (e.g. an anaerobic bacterium) cultured in the cell culture insert; factors for inhibiting the maintenance and proliferation; and factors essential or inhibitory in the symbiosis of the epithelial cells and the bacterium). This means the culture device may contribute to improved efficiency in development of a new bacterial culture method, elucidation of symbiotic mechanisms, isolation and identification of symbiotic factors, or evaluation of foods and medicines.

Further, the culture device of the present disclosure and the culture method using the culture device allows for facilitation of proliferation, isolation and analysis of bacterial flora obtained from the living beings; as well as analysis of multiple specimens of the bacterial flora and a diagnostic method of in vivo environments with results from the analysis.

BRIEF DESCRIPTION OF DRAWINGS

FIG. 1 depicts schematics showing relationship between a culture system for co-culturing of a bacterium (e.g. an anaerobic bacterium) with epithelial cells according to an embodiment of the present disclosure; and an intestinal environment in vivo.

FIG. 2 depicts schematics showing an embodiment of a structure of a culture device for a culture system for co-culturing of a bacterium (e.g. an anaerobic bacterium) with epithelial cells according to an embodiment of the present disclosure.

FIG. 3 depicts a schematic showing an example of a culture device for a culture system for co-culturing of a bacterium (e.g. an anaerobic bacterium) with epithelial cells according to an embodiment of the present disclosure. In the example, culture tanks are communicated with one another.

FIG. 4 depicts a schematic showing an embodiment of a culture device for a culture system of the present disclosure for co-culturing of a bacterium (e.g. an anaerobic bacterium) with epithelial cells. The device has a plurality of openings and a plurality of cell culture inserts to be inserted in the openings are disposed in one culture tank.

FIG. 5 depicts a schematic showing an aspect of a state in co-culturing with a culture system for co-culturing of a bacterium (e.g. an anaerobic bacterium) with epithelial cells according to an embodiment of the present disclosure.

FIG. 6 depicts a schematic showing an aspect of a state in co-culturing with a culture device for a culture system for co-culturing of a bacterium (e.g. an anaerobic bacterium) with epithelial cells according to an embodiment of the present disclosure. The culture system includes a plurality of culture tanks juxtaposed and connected to their neighbors along horizontal axis, in co-culturing of a bacterium (e.g. an anaerobic bacterium) with epithelial cells.

FIG. 7 depicts a schematic showing an aspect of a culture device for a culture system according to an embodiment of the present disclosure, in a state of co-culturing of a bacterium (e.g. an anaerobic bacterium) with epithelial cells. Specifically, the culture device includes one culture tank with a plurality of openings formed therein; and the openings receive cell culture inserts.

FIG. 8 depicts a schematic showing an aspect of a culture device for a culture system according to an embodiment of the present disclosure, in a state of co-culturing of a bacterium (e.g. an anaerobic bacterium) with epithelial cells. Specifically, the culture device includes one culture tank with a plurality of openings formed therein; and the openings receive cell culture inserts. More specifically, the culture device includes large numbers of openings and cell culture inserts; and the culture tank has volume increased so as to maintain gas saturation of a first liquid culture medium when placed in the anaerobic chamber, thereby preventing the medium from turning into anaerobic conditions.

FIG. 9 depicts a schematic showing an aspect of a culture device for a culture system according to an embodiment of the present disclosure, for co-culturing of a bacterium (e.g. an anaerobic bacterium) with epithelial cells. Specifically, the culture device includes a culture tank; and the culture tank has one or more openings in its upper surface part for injecting or changing a first liquid culture medium; and/or for receiving a cell culture insert so as to immerse in the first liquid culture medium, a lower surface of a porous membrane disposed in the bottom of the cell culture insert. The culture device optionally includes one or more additional openings for injecting the first liquid culture medium. Sealing agents are disposed to individually cover one or more openings provided for injecting the first liquid culture medium into the culture tank of the present disclosure, or for changing the medium. This would make the inside of the culture tank airtight.

FIG. 10 depicts a schematic showing an aspect of a structure of a culture device for a culture system according to an embodiment of the present disclosure, for co-culturing of a bacterium (e.g. an anaerobic bacterium) with epithelial cells. Specifically, the culture device includes a culture tank containing a first culture medium; and a cell culture insert is provided to include a tank containing a second culture medium. The cell culture insert further includes a porous membrane in its bottom; and at least one layer of epithelial cells is provided on the upper (inner) bottom surface of the tank containing the second medium. The culture tank has the openings formed therein, one of which receives the cell culture insert so that the bottom of the tank containing the second medium is immersed in the first liquid culture medium. The tank containing the second liquid culture medium includes a plurality of compartments and partition walls of porous membrane structure; and the compartments are separated from one another by the walls.

FIG. 11 depicts a schematic showing an aspect of the culture device for the culture system shown in FIG. 10, which is an embodiment of the present disclosure, in a state of co-culturing of a bacterium (e.g. an anaerobic bacterium) with epithelial cells. Specifically, the tank containing the second culture medium has its bottom of porous membrane structure, as indicated in FIG. 10. The tank further includes a plurality of compartments therein and partition walls of porous membrane structure; and the compartments in the tank are separated from one another by the walls. The compartments allow for parallel co-cultures of different bacteria under anaerobic conditions. Each of the bacteria is allocated in one of compartments, and subjected to co-culture with monolayer of the epithelial cells. Then, each compartment includes a different type of bacteria.

FIG. 12 depicts schematics showing a culture system (I-GOEMON, or Intestinal Germs On Enterocytes-Monitoring) according to an embodiment of the present disclosure, for co-culturing of a bacterium (e.g. an anaerobic bacterium) with epithelial cells; and conventional culture systems under anaerobic conditions ("Anaero"), and under aerobic conditions ("Aero"). This figure schematically indicates that I-GOEMON of the present disclosure maintain oxygen saturation of the first liquid culture medium of the culture tank, at its normal level, i.e. at about 60% after I-GOEMON was placed to stand in the anaerobic chamber. Further, the figure indicates that oxygen saturation in the conventional culture system dropped to 0% after the system was placed to stand under anaerobic conditions (Anaero).

FIG. 13 depicts schematics showing an experimental procedure of co-culturing anaerobic enteric bacteria with intestinal epithelial cells using the culture system (I-GOEMON) and conventional culture systems under anaerobic conditions ("Anaero"), and under aerobic conditions ("Aero"). In this example, the current system I-GOEMON performs co-culturing of a bacterium (e.g. an anaerobic bacterium) with epithelial cells according to an embodiment of the present disclosure.

FIG. 14 depicts a graph showing measurement results of change in oxygen concentration when the following systems were used: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 15 depicts a graph showing results of transepithelial electric resistance (TER) measurements. The measurements were conducted when the following culture systems were used: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 16 depicts a graph showing results of extracellular lactate dehydrogenase (LDH) measurement of when the following culture systems were used: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 17 depicts a graph showing results of intracellular LDH measurements when using the following culture systems were used: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 18 depicts a graph showing results of transepithelial electric resistance (TER) measurements during long-term culturing when the following culture systems were used: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 19 depicts a graph showing the results of extracellular LDH measurements during long-term culturing when the following culture systems were used: I-GOEMON, i.e. the culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 20 depicts a graph showing results (cumulative value) of extracellular LDH measurements in long-term culturing with the following culture systems: I-GOEMON, i.e. a culture system for co-culturing of a bacterium (e.g. an anaerobic bacterium) with epithelial cells according to an embodiment of the present disclosure; and conventional culture systems under anaerobic conditions ("Anaero"), and under aerobic conditions ("Aero").

FIG. 22 depicts a graph showing results of transepithelial electric resistance (TER) measurements against varied compositions of the second liquid culture medium in the cell culture inserts for purpose of investigation of medium conditions for isolation of uncultured and uncultivable enteric bacteria.

FIG. 23 depicts a graph showing results of extracellular LDH measurements against varied compositions of the second liquid culture medium in the cell culture inserts for the purpose of investigation of medium conditions for isolation of uncultured and uncultivable enteric bacteria.

FIG. 25 depicts a graph of experimental results demonstrating that the culture system I-GOEMON as an embodiment of the present disclosure achieved significantly increased proliferation of *Faecalibacterium prausnitzii* as compared to that of a conventional culture method with a culture medium for the bacteria.

FIG. 26 depicts a graph of experimental results demonstrating that by performing a co-culture test using the culture system (I-GOEMON) as an embodiment of the present disclosure and a liquid culture medium for Caco-2 cells to be co-cultured, the measure of the present disclosure achieves significant proliferation of *Faecalibacterium prausnitzii* over prolonged period depending on the cells being co-cultured, without a liquid culture medium optimized individually for the bacterium.

FIG. 27 depicts a graph of experimental results demonstrating that removal of cell layers of Caco-2 cells from the culture system of the present disclosure caused tight junction disruption in aerobic environment of the culture tank, i.e. an environment similar to that at a blood vessel side of intestinal epithelial cell layers.

FIG. 28 depicts a graph showing that gas-impermeable sealing agents in the culture system of the present disclosure was demonstrated to allow for maintenance of high level of oxygen saturation in the culture tank below the cell culture insert during prolonged term, with established proliferation of uncultivable enteric bacteria in the culture system.

FIG. 29 depicts pictures showing immunohistological staining results for studying states of tight junctions observed in the culture system ("I-GOEMON") as an embodiment of the present disclosure for co-culturing of a bacterium (e.g. an anaerobic bacterium) with epithelial cells; and the conventional culture systems under anaerobic conditions ("Anaero"), and under aerobic conditions ("Aero").

DESCRIPTION OF EMBODIMENTS

Figure 21:
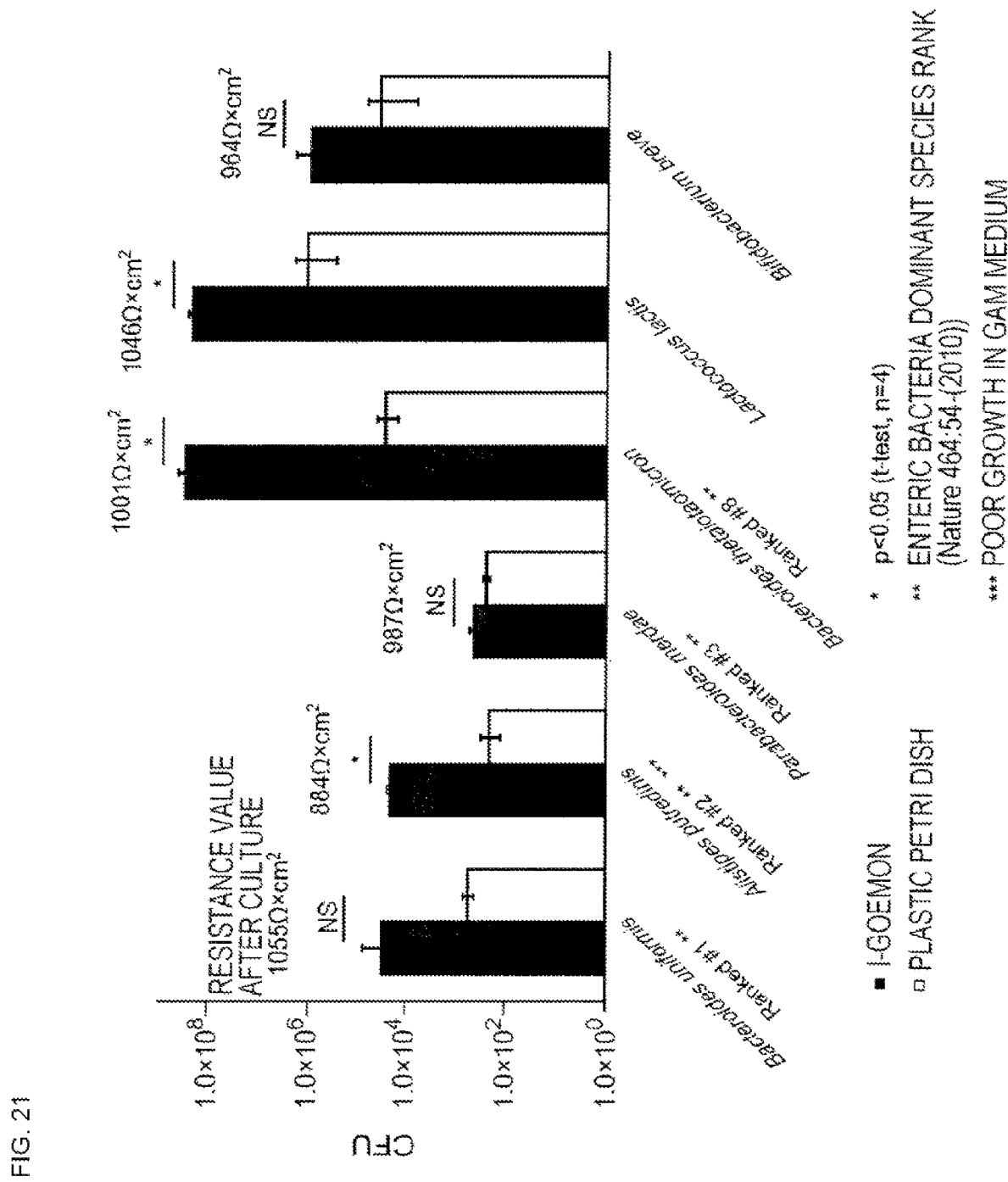
FIG. 21 depicts a graph showing results of transepithelial electric resistance (TER) measurements for confirming growth of various enteric bacteria and a state of intestinal epithelium cell layers when the culture system was used for co-culturing of a bacterium (e.g. an anaerobic bacterium) with epithelial cells according to an embodiment of the present disclosure.

Cultivation of uncultivable obligate anaerobic enteric bacteria in preferable states and analysis of symbiotic relationship of them with intestinal epithelial cells have never been achieved with conventional methodologies of culturing with liquid culture media under anaerobic state, or with co-culturing of enteric bacteria with epithelial cells of the intestinal tract. In the context of the above, Patent Literature 1 then proposed a culture system intended to reflect better actual conditions of naturally occurring intestines. Specifically, the reference read a co-culture system of anaerobic enteric bacteria and monolayer membranes of epithelial cells as configured to prevent disruption of tight junctions between the epithelial cells even under anaerobic conditions.

However, scrutinizing Patent Literature 1 in details reveals the proposed culture system never be considered to meet requirements of culture systems for cultivation of wide variety of enteric bacteria, especially from the viewpoints of versatility, extensibility and high fabricating and running costs although the proposed system may contribute to evaluations in pharmacokinetic studies in intestinal tract in light of maintenance of tight junctions in the system. Specifically, the system of Patent Literature 1 need special dedicated devices for reflecting actual conditions of naturally occurring intestines, including e.g. a microchannel divided by a membrane into two subchannels such that one of the subchannels is located directly above the other cell culture channel; and different fluid sources individually connected to the above subchannels; and vacuum chambers positioned on either side of the microchannel.

Furthermore, the culture system proposed in Patent Literature 1 is configured to receive enteric bacteria in liquid culture media in the microchannel in co-culture of them with epithelial cells. This implies that the culture system cannot retain part of floating enteric bacteria in the microchannel because of culture media continuously flowing into and out of the microchannel. Specifically, enteric bacteria floating in the culture media but not adhered to the intestinal epithelial cells on the porous membrane are likely to flow out of the microchannel even with the bacteria proliferated therein. Therefore, the feasibility of the culture device is limited to culturing some types of the bacteria with ability to get adhered to the intestinal epithelial cells, in the view of efficiency. This means limited versatility of the device. Further, the bacteria flowed out of the microchannel are considered to have disrupted co-culture environment with the intestinal epithelial cells. Therefore, the culture system is considered to provide no accurate characterization of the bacteria in the symbiotic relationship with the epithelial cells because of the above disrupted co-culture environment. The culture system still has problems in view of analysis of symbiotic relationship.

In addition, the culture system of Patent Literature 1 has difficulty in sampling from the microchannel, a fraction of enteric bacteria or epithelial cells or in receiving measuring devices in the microchannel, during the co-culture in the system because of its microchannel's closed structure. In the circumstances, the system of the reference faces obstacles in elucidation of symbiotic relationships among enteric bacteria, or between enteric bacteria and epithelial cells, in intestinal tracts. The system also has difficulty in implementation of limiting dilution of bacteria, multi-wells culture, general-purpose robot-based automation of passage culture.

Conventional anaerobic culture systems have had difficulty in proliferating uncultivable obligate anaerobic bacteria; and some systems contemplated for co-culturing them with epithelial cells have never achieved cultivation of obligate anaerobic bacteria because of disruption of the epithelial cells under anaerobic conditions intended for establishing conditions the obligate the bacteria naturally occur. As stated above, Patent Literature 1 describes allowing for flow of liquid culture media onto intestinal epithelial cells, and for manipulation to repeatedly stretch and relax the porous membrane formed of intestinal epithelial cells, in order to reflect actual conditions of naturally occurring intestines. The reference also suggests those may contribute to maintenance of tight junctions per se between the cells. However, they never be suitable for cultivation of uncultivable obligate anaerobic bacteria. Therefore, the cultivation still remains a problem.

The present inventors assessed various culture conditions for isolating unidentified anaerobic bacteria form living beings in order to identify and characterize them. In a condition for co-culture in liquid culture medium tanks, one of the tanks having enteric bacteria with cells on a porous membrane in the bottom of the tank was maintained under an anaerobic environment of 0% $O_2$, 85% $N_2$, 5% $H_2$, or 10% $CO_2$; and the other tank below the membrane was hermetically sealed. Surprisingly, under the condition, it was found oxygen concentration was maintained in the tanks below the membrane. Furthermore, the above-described culture condition was found to allow for maintenance for 5 or more days of tight junctions between epithelial cells in preferable condition even under anaerobic condition in the culture tanks. In this regard, it is around every five days that intestinal epithelial cells renew themselves with new cells. Then, although conventional culture conditions still have difficulty in growth of enteric bacteria (e.g. *Bacteroides* eubacteria such as *Alistipes putredinis*); the present inventors found that highly efficient growth of enteric bacteria was established with the above co-culturing condition, i.e. co-culturing of anaerobic enteric bacteria with epithelial cells in the liquid culture medium tank under the anaerobic environment. The results contributed to our achievement of the disclosure. Further, we assessed various compositions of liquid culture media used for co-culturing to demonstrate usefulness of the system for identifying compositions suitable or unsuitable for uncultivable anaerobic enteric bacteria; or searching for factors contributing to such compositions. The assessments contributed to our achievement of the disclosure. Furthermore, we also have achieved remarkable proliferation of *Faecalibacterium prausnitzii* with our co-culturing in anaerobic state although the bacterium had been known as uncultivable even with epithelial cells and as a useful intestinal bacterium in humans, animals, poultry and the like.

A measure of the present disclosure will be described below with reference to the drawings as appropriate.

As used herein, the term "anaerobic condition" refers to a condition where oxygen is present in the medium at low concentration or no oxygen is present in the medium. In another embodiment, oxygen concentration set in "anaerobic condition" may fall within a range varying in accordance with types of cells treated under the anaerobic condition, and such range may be suitably specified by those skilled in the art. For example, in some embodiments of the present disclosure, the "anaerobic condition" refers to a condition where oxygen concentration in air ranges from 0% to 5%, but is not limited thereto. Meanwhile, as used herein, "aerobic condition" refers to a condition where oxygen is present in the medium at high concentration or all the medium is oxygen. In another embodiment, oxygen concentration set in "aerobic condition" may fall within a range varying in accordance with types of cells treated under the aerobic condition, and may be suitably specified by those skilled in the art. For example, in some embodiments of the present disclosure, the "aerobic condition" is achieved with 60% saturation of the dissolved oxygen concentration in the liquid culture medium, but this is merely an example, and is not limited thereto. Again, those skilled in the art using the culture system of the present disclosure can appropriately determine conditions such as oxygen concentration or the like, by suitably referring to the disclosure of the present specification, depending on their purpose.

As used herein, "a first cell group consisting of one or more kinds of cells" means a cell group formed of one or plural kinds of cells, including various cells capable of surviving under anaerobic conditions (e.g., oxygen concentration of less than 5%, including 0%) in addition to obligate anaerobic bacteria, anaerobic bacteria and aerobic bacteria capable of surviving under anaerobic conditions (e.g., oxygen concentration of less than 5%, including 0%).

As used herein, "a second cell group consisting of one or more kinds of cells different from the former cells" means a cell group forming a cell layer or a tissue co-cultured with the first cell group in the culture system in the measure of the present disclosure. These cell groups are cell groups fainted of one or plural kinds of cells. Examples of cells forming the cell groups may include, in addition to cells forming the epithelium. Caco-2 cells, HT29 cells, T84 cells, primary intestinal epithelial cells, follicular cells, M cells (microfold cells), goblet cells (mucus production), endocrine cells, mucosal secretory cells, crypt cells, paneth cells, intestinal epithelial stem cells, or the like, cells obtained by inducing differentiation from iPS cells, ES cells or other cells so that the cells can exert function of cells forming intestinal epithelium, cells obtained by inducing differentiation from various epithelial cells such as intestinal epithelial cells, oral epithelial cells, vaginal epithelial cells and the like, iPS cells, ES cells and other cells so that the cells can exert function of cells forming epithelium, but the cells are not limited thereto.

As used herein, "first culture tank" refers to a culture tank for co-culturing the above-described first cell group with the cell layer or tissue formed in the second cell group under anaerobic conditions. In the tank of the first culture tank, the above-described first cell group and the cell layer or tissue formed of the second cell group are contained together with the liquid culture medium under anaerobic conditions and/or gas under anaerobic conditions. Here, as will become apparent from the other description in the present specification, the term "cell culture insert" corresponds to the above-described "first culture tank", and an exemplary specific shape thereof is shown in FIGS. 1 to 11 (in each drawing, this member is shown as a cell culture insert (2)). Further, the "cell culture insert" may function as a "substance-exchange structure" described below in a bottom part of the cell culture insert.

As used herein, the term "second culture tank" refers to a culture tank for pooling a liquid culture medium of aerobic conditions. In some embodiments, the culture tank is a tank for pooling a liquid culture medium having an aerobic condition equal to or higher than a predetermined oxygen saturation. Here, the oxygen saturation is, for example, an amount corresponding to oxygen saturation in capillaries existing in the vicinity of epithelial cells (e.g., intestinal epithelial cells, oral epithelial cells, vaginal epithelial cells). In addition, components or dissolved gas components (e. g., oxygen and the like) contained in the liquid culture medium of aerobic conditions can move to a first culture tank side through the substance-exchange structure (e.g., porous membrane (3)). In an exemplary embodiment of the present disclosure, a cell layer or tissue is disposed on the surface on the first culture tank side of the substance-exchange structure, and thus this cell layer or the like can exchange substances (dissolved components) between the first culture tank and the second culture tank.

As used herein, "substance-exchange structure" refers to a permeable structure positioned between the first culture tank and the second culture tank for co-culturing the first cell group with the cell layer or tissue formed in the second cell group. The structure divides the spaces defined by the first culture tank and the second culture tank into subspaces (compartments). The structure is permeable to liquid culture media, and components dissolved therein, allowing for the transport or exchange of them through the structure between the compartments. Specifically, the substance-exchange structure refers to a structure capable of exchanging a liquid culture medium or a component dissolved in the liquid culture medium, dissolved gases, biological components derived from the cell layer or a tissue between compartments of the spaces separated by the structure; while proliferating the cell layer or the tissue aimed in the first culture tank on the surface of the structure and maintaining shapes of the cells in the cell layer or tissue sufficient to retain their functions (e.g. proliferating the cells while avoiding two-dimensional extension-mediated damages to the original shapes of the cells). More specifically, the substance-exchange structure is a structure intervening at interface between a first culture tank and a second culture tank and connected to both of the tanks, configured to deliver components in one of the tanks via the structure to the other, and vice versa. That is, components or dissolved gases contained in a liquid culture medium of aerobic conditions pooled in the second culture tank are delivered through the structure to the first tank including the cell layer or tissue with the delivered components filtrated to the cells. On the other hand, biocomponents or dissolved gases secreted from the cell layer or tissue in the first culture tank are delivered through the structure to the second culture tank.

This structure may have any shape as long as the conditions described above are satisfied, and may include, for example, a wall, a membrane, a thin membrane, or a film. Furthermore, this structure may have a pore size enough to hold the cell layer or tissue in the first culture tank. This structure may be, in some embodiments, a porous, membrane-like structure including the structure formed of resin such as polytetrafluoroethylene or the like, but is not limited thereto. A pore size of the porous structure is, in some embodiments, about 0.2 to 10 µm, in another embodiment, 0.2 to 0.5 µm, and in yet another embodiment, 0.4 µm, but is not limited thereto. In the accompanying drawings, a porous membrane (3) is disclosed as an example of the substance-exchange structure.

As used herein, "tight junction" refers to a cell-to-cell combination at the most top end side of the cell.

As used herein, the term "gas-impermeable sealing agent" refers to an agent or member used for the purpose of sealing a gap or space gases can escape from. In some embodiments of the present disclosure, a sealing agent may be applied to openings between the second culture tank and the first culture tank (e.g., not only a hole intentionally provided in a wall between the first and second culture tanks but also a gas-permeable gap between connecting or mating surfaces in openings of the first culture tank and the second culture tank), thereby sealing gap or openings and making the inside of the second culture tank in a closed state. Examples of the above-described sealing agent may include, but not limited to, a gas-impermeable caulking agent or silicone grease to be used by coating, a vinylidene fluoride (FKM)-based rubber such as Viton fluororubber used as packing or cap, and the like.

As used herein, a "gas-permeable moisturizing member" is a member that allows only a certain gas to permeate while sealing a portion of the second culture tank that is open to the outside (the environment). By providing this member, the inside of the first culture tank is maintained in an anaerobic state while preventing the inside of the first culture tank from being dried but moisturizing the first culture tank, thus contributing to keeping the shape and function of the first cell group and the cell layer or tissue formed in the second cell group maintained in the first culture tank. In some embodiments of the present disclosure, the moisturizing member may be used in a state where there is no opening to the outside (the environment) other than a portion to which the moisturizing member is applied (i.e., a portion through which a certain gas is permeated while being sealed by the moisturizing member). Examples of gas-permeable moisturizing members may include an adhesive film material such as a gas-permeable moisturizing barrier seal, a moisturizing plate cover for culture plate, but the gas-permeable moisturizing member is not limited thereto.

Further, the second culture tank pooling the liquid culture medium of aerobic conditions in the present disclosure is a structure corresponding to a culture tank (1) in the attached drawings. In an exemplary embodiment, the culture tank (1) has an opening (1a). The opening may be provided besides the opening for receiving the cell culture insert (2) (e.g., see FIG. 9).

Described are shapes, constitutions, and materials for the culture systems of the present disclosure for co-culturing of a bacterium (e.g. an anaerobic bacterium) with epithelial cells when the system in use is placed in an anaerobic chamber.

In an embodiment of the present disclosure, provided is the culture system for co-culturing of a bacterium (e.g. an anaerobic bacterium) with epithelial cells in a state where the culture system is placed in the anaerobic chamber. In this embodiment, the culture system includes, as shown in FIG. 1, a culture tank (1) having the opening (1a), i.e., a second culture tank for pooling the liquid culture medium of aerobic conditions; a cell culture insert (2) having a porous membrane (3), i.e., a substance-exchange structure in the bottom surface, and at least one layer of epithelial cells (6) on the porous membrane of the cell culture insert; a gas-impermeable sealing agent (4), and a gas-permeable moisturizing member (5).

The culture tank (1) is made of a gas-impermeable material, and includes at least one or more tanks for pooling a liquid culture medium of aerobic conditions (7) in the tank under gas-impermeable and closed conditions, and at least one or more openings (1a), which are provided at an upper surface part, for injecting/exchanging the liquid culture media of aerobic conditions, and/or for receiving the cell culture insert so that the lower surface of the porous membrane in the bottom of the cell culture insert is immersed in the liquid culture medium of aerobic conditions (FIGS. 1 to 11). Injection/replacement of the liquid culture media under aerobic conditions and insertion of the cell culture insert may be performed through the same opening, and may be performed through separate openings provided for each (FIGS. 9 to 11). Further, one or more openings may be provided for optionally injecting/exchanging the liquid culture media of aerobic conditions.

The culture tank (1) has a size of an opening into which a general-purpose cell culture insert can be inserted, and the size of the tank itself is set to be larger than the opening (FIG. 1). When the opening for addition of the liquid culture medium is provided separately, the size of the tank itself is set to be much larger than those of the openings (FIG. 9).

In addition, as shown in FIG. 3, a plurality of tanks may be connected, and in this case, the tanks connected in a multi-plate shape are preferable since it is easy to handle and it is compatible with automation work. In performing limiting dilution from a bacteria mixed culture, the plurality of tanks is preferable because it is easier to perform operations of diluting and inoculating bacteria in the adjacent cell culture insert as shown in FIG. 6.

Furthermore, as shown in FIGS. 4 and 8, the culture tank (1) may have a shape for receiving a plurality of cell culture inserts (2). This configuration, especially, the inserts sharing the culture tank (1) as their receiver, allows for simultaneously culturing different types of bacteria with environments reproducing viable bacterial flora. Further, a stirrer bar may be placed in the liquid culture medium of aerobic conditions in the culture tank (1) to agitate gently the medium, thereby causing uniform distributions of not only the culture medium but also components flowed through the porous membrane from epithelial cells. As described above, the system of the present disclosure is adjustable for target symbiotic states of the bacterial flora with the epithelial cells in vivo, thereby reproducing symbiotic or co-culture environments in better manner.

A material used for the culture tank (1) includes, but not limited to a material generally used in members for cell culture. For example, the material may be resin materials with thickness sufficient for maintaining gas impermeability, including e.g. polystyrene, polyethylene terephthalate (PET), polypropylene, polycarbonate, polyamides (e.g. nylon) and the like; various metals (e.g., stainless steel including SUS304) and the like. In addition, some resin materials are themselves oxygen-permeable due to their small thickness but such resin materials may be subjected to additional treatment for producing gas-impermeable layers or films thereon (e.g. lamination) before the materials are used for the tank. Such layers or films includes vapor-deposited films of silicon oxide, aluminum oxide, aluminum or the like; aluminum foils; or resin films of polyethylene naphthalate, polyvinylidene chloride, an ethylene vinyl copolymer, polyvinyl alcohol, or the like.

In addition, the cell culture insert (2) is provided with a porous membrane (3) in the bottom; and at least one layer of epithelial cells is provided on the porous membrane in its upper surface. The opening of the culture tank receives the cell culture insert with the porous membrane (in outer or lower surface) immersed in the liquid culture medium of aerobic conditions (FIGS. 1 to 10). This porous membrane can be made of a resin such as polytetrafluoroethylene. The membrane also has a pore size sufficient to hold the epithelial cells provided thereon. More specifically, the membrane has the pore size of about 0.2 to 10 µm, preferably 0.2 to 0.5 µm, and more preferably 0.4 µm.

In the cell culture insert (2), the tank including the porous membrane in the bottom for pooling second liquid culture medium may further optionally be divided by partition walls having a porous membrane to form a plurality of compartments (FIGS. 10 and 11), and the pore size in the partition walls may be different from that in the bottom surface. This porous membrane is made of a resin (e.g., polytetrafluoroethylene) and has a pore size sufficient to prevent enteric bacteria for culture from passing through the membrane. Preferably, the membrane has a pore size of about 0.1 to 0.5 µm or preferably, 0.2 µm. The cell culture inserts share the culture tank (1) as their common receiver, and allow for simultaneously culturing different types of bacteria and for diffusion of the second liquid culture medium through the porous membranes (3). Consequently, the configuration allows for environments reproducing viable bacterial flora and symbiotic environments with layers of epithelial cells. It is preferable.

In addition, at least one layer of epithelial cells (6) are provided on the porous membrane of the cell culture insert. The layer of epithelial cells in the measure of the present disclosure may be any cell sheet of epithelial cells, especially in form of a sheet including a monolayer or layers of the cells.

The cells used in the measure of the present disclosure may be Caco-2 cells, HT29 cells, T84 cells, primary intestinal epithelial cells, follicular cells, M cells (microfold cells), goblet cells (mucus production), endocrine cells, mucosal secretory cells, crypt cells, paneth cells, intestinal epithelial stem cells or the like; intestinal epithelial-like cells differentiated from iPS cells, ES cells or other cells. Further, in addition to the intestinal epithelial cells, the following cells may be used: various epithelial cells such as oral epithelial cells, and vaginal epithelial cells, and epithelial-like cells differentiated from iPS cells, ES cells or other cells. Then, a single type of these cells may be cultured, and further, a mixture of two or more types of these cells may be used for co-culture.

These cells can be passaged with conventional methods including pre-culture, trypsin treatment, resuspending in a liquid culture medium, and inoculating on a culture plate or the like. The liquid culture medium may be not only any cell culture medium generally used in the art, but also a medium optimized for culture and differentiation. For example, a basal medium may be used depending on types of cells used, including for example, MEM, BME, DMEM, αMEM, IMDM, ES medium, DM-160 medium, Fisher medium, F1 medium, WE medium, RPMI 1640 medium, or the like. In addition, the following may be added to the basal medium: serum (e.g., fetal calf serum), various growth factor(s), antibiotic(s), amino acid(s), and the like. Further, serum-free media can be used.

The gas-impermeable sealing agent (4) is made of a gas impermeable material, and is disposed at the opening (1a) of the culture tank and a gap formed between the opening (1a) of the culture tank and the cell culture insert (2) so that the inside of the culture tank (1) is in a gas-impermeable closed state. The gas impermeable material includes, but not limited to, a generally available gas impermeable material.

The following may be used for application: a caulking agent such as Bathcoke N-clear (semi-transparent) (CEMEDINE Co. Ltd., Japan), silicone grease or the like. Preferably, vinylidene fluoride (FKM)-based rubber such as Viton fluorine rubber (Chemours Company, USA) may be used as gasket or plug, thereby enhancing operating efficiency.

In addition, the moisturizing member (5) is optionally provided so as to block evaporation of the second culture medium contained in the cell culture insert. Specifically, the moisturizing member (5) may cover any opening in top surfaces of the cell culture insert and of the culture tank receiving it in the opening. The moisturizing member may include an adhesive film material such as gas-permeable moisturizing barrier seal (4titude, UK) or a moisturizing plate cover for culture plate. Such a film material may allow for prevention of contamination in adjacent cell culture inserts or culture systems by bacteria in culture due to aerosol generation during passage operation. Further, even with the film attached, bacteria in the culture can be easily collected by metal pickers, from the cell culture insert. Thus, the system is easily compatible with automation. Further, co-culture of a bacterium (e.g. an anaerobic bacterium) with epithelial cells may be conducted without the moisturizing member (5) in an environment in the anaerobic chamber of a humidity sufficient to prevent evaporation of the second liquid culture medium from the cell culture insert.

In addition, since the culture system of the present disclosure performs co-culturing of a bacterium (e.g. an anaerobic bacterium) with epithelial cells in the state where the culture system is placed in an anaerobic chamber, it is necessary to prepare an anaerobic chamber at the time of use. The anaerobic chamber may be an anaerobic chamber commonly used in this field such as a gas mixing system that can form a hypoxic and anoxic state (e.g., Hypoxia Workstation INVIVO2 400 (Ruskinn Technology Ltd. UK) provided with I—CO2N2IC (Ruskinn Technology Ltd)) and the like. The oxygen concentration in the anaerobic chamber may be, in some embodiments, less than 5% (including 0%), in another embodiment 0 to 4%, in another embodiment 0 to 3%, in yet another embodiment 0 to 2%, in still another embodiment 0 to 1%, and in still another embodiment 0%.

In some embodiments of the present disclosure, the culture system is provided with a state where components other than cells are sterilized in advance. The liquid culture medium may be sterilized by sterilization techniques widely used in this field such as filter sterilization, autoclave sterilization, and the like. Further, a method for sterilizing a container for bacteria culture includes, but not limited to, a method commonly used as a method for sterilizing a container for cell culture. For example, the following may be used: ethylene oxide gas sterilization, γ-ray irradiation sterilization, electron beam sterilization, radiation sterilization, ultraviolet irradiation sterilization, hydrogen peroxide sterilization, and ethanol sterilization. Further, in consideration of easiness of production and cost reduction, ethylene oxide gas sterilization, electron beam sterilization or γ-ray irradiation sterilization is preferably used as the sterilization method. The electron beam sterilization is performed to the extent that the container for bacterial culture is not deteriorated. The γ-ray irradiation energy in the γ-ray irradiation sterilization preferably ranges from 5 to about 30 kGy so as to sterilize the container for enteric bacteria culture to such an extent that the container is not deteriorated.

Bacteria such as anaerobic bacteria in the present disclosure are bacteria that are coexisting in human and animal bodies and bacteria capable of coexisting in human and animal bodies, and include anaerobic bacteria and aerobic bacteria that are capable of surviving under anaerobic conditions of less than 5% (including 0%), in addition to obligate anaerobic bacteria.

With respect to the culture method for co-culturing of a bacterium (e.g. an anaerobic bacterium) with epithelial cells using the above-described culture system for co-culturing of the bacterium such as an anaerobic bacterium with epithelial cells in a state where the culture system is placed in the anaerobic chamber of the present disclosure.

Co-culture of bacteria such as anaerobic bacteria or the like with epithelial cells may be performed by using above-described the culture system for co-culturing of a bacterium (e.g. an anaerobic bacterium) with epithelial cells in a state where the culture system is placed in the anaerobic chamber of the present disclosure.

The procedure is described as follows.

First, the epithelial cells (6) with the liquid culture medium are inoculated on an upper surface of the porous membrane (3) disposed in the bottom of the cell culture insert (2) in the above-described culture system for co-culturing of a bacterium (e.g. an anaerobic bacterium) with epithelial cells in a state where the culture system is placed in the anaerobic chamber of the present disclosure, thereby forming at least one layer of epithelial cells on an upper surface of the porous membrane (3).

Next, the liquid culture medium (7) under aerobic conditions is injected from the opening (1a) of the culture tank (1) in the above-described culture system for co-culturing of a bacterium (e.g. an anaerobic bacterium) with epithelial cells in a state where the culture system is placed in the anaerobic chamber of the present disclosure.

Then, the cell culture insert in which at least one layer of epithelial cells is formed on the upper surface of the porous membrane is placed in the opening of the culture tank (1) so that the lower surface of the porous membrane is immersed in the liquid culture medium under aerobic conditions.

Then, the culture tank (1) in this culture system is allowed to be closed by the gas-impermeable sealing agent (4). In addition, the above-described entire culture system is placed in the anaerobic chamber.

Further, the medium in the cell culture insert is replaced with the second liquid culture medium (which is a liquid culture medium that is anaerobically treated in advance). Bacteria such as anaerobic bacteria are added to the second liquid culture medium (8) in this cell culture insert.

In the operation in the preceding paragraph, replacing the medium in the cell culture insert (2) may be performed by using a suspension of anaerobic bacteria in the second liquid culture medium (8).

Then, the gas-permeable moisturizing member (5) is attached to a portion exposed to the external environment of the culture tank to prevent evaporation of water.

EXAMPLES

Hereinafter, there are provided Examples of manufacturing a culture system capable of coculturing a bacterium (e.g. an anaerobic bacterium) with epithelial cells; and using the culture system in an anaerobic chamber, as indicated in the present disclosure. The present disclosure is not limited to those following particulars.

As described in "Description of Embodiment", we have manufactured a culture system of the present disclosure for co-culturing a bacterium (e.g. an anaerobic bacterium) with epithelial cells in the state where the culture system is placed to stand in a anaerobic chamber. Specifically, as an embodiment of the present disclosure, the culture system (FIGS. 1 and 2) includes a first culture tank, a substance-exchange structure, epithelial cells, a second culture tank, a gas-impermeable sealing agent, and a gas-permeable moisturizing member. In use, the culture system is placed to stand in a anaerobic chamber, and this will allows for co-culturing of a bacterium with epithelial cells. The first culture tank includes one or more substance-exchange structures provided in the bottom surface and at least one layer of the epithelial cells disposed to cover the upper surface of the substance-exchange structures. The second culture tank includes a tank for pooling a liquid culture medium under aerobic conditions; and one or more openings in the upper surface part of the tank. The openings are provided for exchanging and pooling the liquid culture medium under the aerobic conditions, and for receiving the first culture tank. The openings formed in the second culture tank receive the first culture tank so that the bottom of the first culture tank containing the first medium is immersed in the culture medium pooled in the second culture tank under aerobic condition. The gas-impermeable sealing agents are provided to gaps between the inserted first culture tank and the second culture tank at their contact sites so that the inside of the tank become in a hermetically closed state. Further, the members also apply to the openings provided in the second culture tank for adding or exchanging liquid culture media of aerobic condition. This allows for making the inside of the second culture tank in a hermetically closed state. The gas-permeable moisturizing member seals the opening that receives the first culture tank during co-culturing, and the first culture tank is maintained under anaerobic condition. We outsourced manufacturing of the culture system to WakenBtech Co., Ltd. (Japan), and SUS304 stainless steel was used as a material of the culture tank. A porous membrane having a pore size of 0.4 μm (ThinCert™ Tissue Culture Inserts for Multiwell Plates (12 wells), Cat. No. 665 641, Greiner, Germany) was used for the porous membrane provided in the bottom of the cell culture insert. Bathcoke N-clear (semi-transparent) (CEMEDINE CO., LTD, Japan) was used as the gas-impermeable sealing agent. Gas-permeable moisturizing barrier seals (4titude, UK) were used as the gas-permeable moisturizing member. The anaerobic chamber was used for experiments with the following setting, i.e. the anaerobic environment of 0% $O_2$, 85% $N_2$, 5% $H_2$, and 10% $CO_2$ using Hypoxia Workstation INVIVO2 400 (RUSKINN TECHNOLOGY, UK) provided with a gas mixing system I—CO2N2IC (Ruskinn Technology Ltd)).

The present culture system as manufactured in accordance with the above descriptions, co-cultures a bacterium (e.g. an anaerobic bacterium) with epithelial cells when placed in an anaerobic chamber. The system is intended to reflect actual environments in the intestines of human or animals. More specifically, the anaerobic chamber provides anaerobic environments. Illustrative anaerobic environments established in the anaerobic chamber include, but not limited to an atmosphere of 0% $O_2$, 85% $N_2$, 5% $H_2$, and 10% $CO_2$. Such an anaerobic environment is intended to reflect anaerobic environments in the intestinal lumen throughout the length of intestinal tract. In this regard, the culture system includes a tank having a porous membrane in its bottom and at least one layer of epithelial cells thereon. The tank is received by an opening formed in another culture tank of the system so that the inserted tank is immersed in a culture medium of aerobic condition pooled in the receiving tank. The inserted tank has the porous membrane in the bottom and the monolayer of epithelial cells, as stated above; and the tank further contains a second culture medium on the monolayer. The inserted tank optionally includes partition walls of porous membrane structure, which subdivide the inside of the tank into compartments. Then, the system has at least one layer of epithelial cells as described above, and the cells are on porous membrane structure in the bottom of the tank, i.e. cell culture insert(s). As a whole, these reflect conditions of epithelial cells in intestines, i.e. they are partially under aerobic environment, specifically in their sides of lamina propria sides containing blood vessels; and partially under anaerobic environment. Further, the gas-impermeable sealing agent contributes to establishment of the anaerobic environment, i.e. the member is made of a gas-impermeable material and disposed at openings of the culture tank and at gaps between the cell culture insert and the tank receiving the insert so that the inside of the culture tank become in hermetically closed state. On the contrast, in order to reflect aerobic environment of the lamina propria sides containing blood vessels, the culture tank per se is made of a gas impermeable material, and contains the liquid culture medium under hermetically closed condition. Then, the tank has at the upper surface thereof, at least one or more openings for injecting the liquid culture medium of aerobic conditions, and/or for receiving the cell culture insert so that the lower surface of the porous membrane disposed in the bottom of the cell culture insert is immersed in the liquid culture medium of aerobic conditions (FIG. 1).

Therefore, the present inventors named the culture system of a bacterium (e.g. an anaerobic bacterium) with epithelial cells, which is an embodiment of the present disclosure, as Intestinal germs on enterocytes-monitoring chamber, and referred as I-GOEMON-chamber or I-GOEMON as abbreviation, and confirmed that this embodiment of the present disclosure, the culture system of I-GOEMON could be used as a co-culture system which imitates a symbiotic environment as expected.

Experimental Example 1

Changes in oxygen concentration were studied by using the culture system (I-GOEMON) for co-culturing of a bacterium (e.g. an anaerobic bacterium) with epithelial cells, which is an embodiment of the present disclosure; and the conventional culture systems under anaerobic conditions ("Anaero") and under aerobic conditions ("Aero").

By the procedure illustrated in FIG. 13, Caco-2 cells were inoculated on the upper surface of the porous membrane disposed in the bottom surface of the cell culture insert, and Caco-2 cells become differentiated and polarized to become a substantially monolayer, and to form tight junctions. Firstly, DMEM (high Glc; 10% FBS+penicillin/streptomycin (hereafter, "P/S")) was used to inoculate Caco-2 cells at $2 \times 10^5$ cells/well in the cell culture insert of the culture system "I-GOEMON" of the present disclosure. Secondly, the cell culture inserts were set in cell culture dishes. The cells were cultured in $CO_2$ cell culture incubators. DMEM (high Glc; 10% FBS+P; S) for monolayered Caco-2 cells in the cell culture insert and in cell culture dishes were replaced every 2 to 3 days. The Caco-2 cells became differentiated and polarized to form a substantially monolayer and to form tight junctions. DMEM (high Glc: 10% FBS+P/S) for the monolayered Caco-2 cells, which have undergone the regular culture, was replaced with the same medium without antibiotics.

Then, the culture systems with the following setting have been used, and each culture tank of the systems included the cell culture insert on which the Caco-2 cell layers were formed: I-GOEMON as an embodiment of the present disclosure; and the conventional culture systems under anaerobic conditions ("Anaero") and under aerobic conditions ("Aero"), where each of their culture tanks was not sealed. In this regard, I-GOEMON i.e. the culture system for co-culturing of a bacterium (e.g. an anaerobic bacterium) with epithelial cells was provided to include the culture tank and the second culture tank. The culture tank was set in a gas impermeable state established with gas-impermeable sealing agents; and the second culture tank was provided to include the moisturizing member disposed thereon. The culture system I-GOEMON was placed in the anaerobic chamber under an anaerobic environment of 0% $O_2$, 85% $N_2$, 5% $H_2$, and 10% $CO_2$. Then, oxygen concentration of the liquid culture medium in the culture tank and the cell culture insert was measured using a non-destructive needle type oxygen transmitter Microx TX3 (Micro fiber optic oxygen transmitter, PreSens).

As a result, surprisingly, as shown in FIG. 14, when using an embodiment of the present disclosure, i.e. the culture system (I-GOEMON) for co-culturing of the bacterium (e.g. an anaerobic bacterium) with epithelial cells, oxygen concentration of the liquid culture medium under aerobic conditions in the culture tank was maintained at 60% or more saturation for at least 5 days. Meanwhile, in all of the liquid culture medium exposed to the anaerobic environment, oxygen concentrations were reduced to 0.1-0.3% saturation within one day.

The results demonstrate that just placing in the anaerobic chamber, the culture system I-GOENON of the present disclosure for co-culturing of a bacterium (e.g. an anaerobic bacterium) with epithelial cells allows for at least five-day maintenance of anaerobic and aerobic environments in the cell culture insert and in the culture tank, respectively. In this regard, the anaerobic and aerobic environments are established to reflect actual environments of intestinal lumen in the intestinal tract, and the blood vessel side of the intestinal epithelial cell layer, respectively. This implies that the current system is considered to meet desired requirements for new generation systems for co-culturing of a bacterium (e.g. an anaerobic bacterium) with epithelial cells.

Experimental Example 2

Further, experiments were conducted to evaluate the states of intestinal epithelial cells when cultured using I-GOEMON, an embodiment of the present disclosure.

The same protocol as that in the above Experimental Example applied to culturing processes in this Example. Specifically, the epithelial cells were inoculated and differentiated to monolayer on the upper surface of the porous membrane disposed in the bottom surface of the cell culture inserts; and the culture systems with the following setting have been used, and each culture tank of the systems included the cell culture insert having the epithelial cell layer thereon: I-GOEMON as an embodiment of the present disclosure; and the conventional culture systems under anaerobic conditions ("Anaero") and under aerobic conditions ("Aero"), where each of their culture tanks was not sealed. During co-culturing, I-GOEMON and the conventional culture system ("Anaero") were placed to stand in an anaerobic chamber; on the other hand, the conventional culture system ("Aero") was placed to stand in a $CO_2$ incubator. Then, transepithelial electrical resistance (TER), extracellular lactate dehydrogenase (LDH) activity, and intracellular LDH activity were measured.

Transepithelial electric resistance (TER) measurement can evaluate the degree of maintenance of the barrier function by the tight junction of cells. TER was measured by placing electrodes in apical and basolateral surfaces of the monolayers of epithelial cells cultured in the cells culture inserts. The tight junctions of epithelial cells (e.g. intestinal epithelial cells) exclude some ions but allow for the passage of other ions between apical and basolateral surfaces of the monolayers of the epithelial cells, thereby generating TER between the surfaces. Therefore, TER values can be used as indicators for evaluating the barrier function by the tight junctions. Sufficiently high TER measured values indicate maintenance of barrier function of the epithelial cells monolayer-cultured in the cell culture insert. Meanwhile, low TER measured values indicate some factor-mediated damaged states of barrier function of monolayers of epithelial cells cultured in the cell culture inserts. TER measurements were made using Milicell ERS (Millipore), a TER measuring device.

Further, liquid culture media were collected from the cell culture insert, and the extracellular lactate dehydrogenase (LDH) activity was measured with Cytotoxicity LDH Assay Kit (DOJINDO LABORATORIES, Japan). The lower and higher values of the measured activities would indicate good and damaged condition of the cells, respectively.

Further, intracellular LDH activities were measured with Cytotoxicity LDH Assay Kit (DOJINDO LABORATORIES, Japan), specifically as follows: collecting Caco-2 cells, washing the cells with PBS, and then dissolving the cells with the kit's lysis solution to measure the activities. The higher and lower values of the measured activities would indicate good and damaged conditions of the cells, respectively.

For each of the above measurements, "Day 0" was defined as the day of the culture start. Five biological replicates were conducted for each experiment condition on "Day 0" and each day of five consecutive days ("Days 1, 2, 3, 4, and 5") after the culture start.

As a result, it was found that in the conventional culture systems under anaerobic conditions ("Anaero"), on Day 3 or later, the tight junction-medicated barrier function of monolayered Caco-2 cells was destroyed and the cells themselves were also damaged. Meanwhile, I-GOEMON as an embodiment of the present disclosure, was demonstrated to maintain for 5 days during co-culturing, the tight junction-mediated barrier function of the monolayered Caco-2 cells in the state preferable to the same extent as that under aerobic condition. The co-culturing was conducted by simply placing in an anaerobic chamber, the culture system for co-culturing of a bacterium (e.g. an anaerobic bacterium) with epithelial cells (FIGS. 15 to 17).

Experimental Example 3

Further, experiments were conducted to evaluate the state of intestinal epithelial cells when cultured with I-GOEMON for a longer period of 12 days.

The same protocol as that in Experimental Example 2 applied to culturing processes in this Example. Specifically, the epithelial cells were inoculated and differentiated to monolayer on the upper surface of the porous membrane disposed in the bottom surface of the cell culture inserts; and the culture systems have been used with the following settings, and each culture tank of the systems included the cell culture insert having the epithelial cell layer thereon: I-GOEMON as an embodiment of the present disclosure; and the conventional culture systems under anaerobic conditions ("Anaero") and under aerobic conditions ("Aero"), with each of their culture tanks not sealed. During co-culturing, I-GOEMON and the conventional culture system ("Anaero") were placed to stand in an anaerobic chamber; on the other hand, the conventional culture system ("Aero") was placed to stand in a $CO_2$ incubator. Culture media were replaced every 4 days in the cell culture inserts and the culture tanks. Then, transepithelial electrical resistance (TER), extracellular lactate dehydrogenase (LDH) activity, and intracellular LDH activity were measured.

As a result, it was found that in the conventional culture systems under anaerobic conditions ("Anaero"), on Day 4 or later, the tight junction-medicated barrier function of monolayered Caco-2 cells was destroyed and the cells themselves were also damaged. Meanwhile, I-GOEMON as an embodiment of the present disclosure, was demonstrated to maintain for 12 days during co-culturing, the tight junction-mediated barrier function of the monolayered Caco-2 cells in the state preferable to the same extent as that under aerobic condition. The co-culturing was conducted by simply placing in an anaerobic chamber, the culture system for co-culturing of a bacterium (e.g. an anaerobic bacterium) with epithelial cells (FIGS. 18 to 20).

From these results, in co-culturing of a bacterium (e.g. an anaerobic bacterium) with epithelial cells, the culture system I-GOEMON as an embodiment of the present disclosure was demonstrated to maintain the tight junction-mediated barrier function of the cells and to reflect better the actual intestinal environments even if the intestinal epithelial cells were continuously maintained in an anaerobic environment such as 0% $O_2$, 85% $N_2$, 5% $H_2$, and 10% $CO_2$ for a longer period of time. Therefore, an additional test was performed to confirm whether this I-GOEMON culture system was useful in co-culture with a bacterium (e.g. an anaerobic bacteria) as indicated in the following sections.

Experimental Example 4

The co-culture test with an anaerobic bacterium was performed using the culture system (I-GOEMON) as an embodiment of the present disclosure for co-culturing of a bacterium (e.g. an anaerobic bacterium) with epithelial cells.

Enteric bacteria were obtained from National Research and Development Agency "RIKEN", the Institute of Physical and Chemical Research, Bio Resource Center (Tsukuba, Japan). Specifically, the obtained enteric bacteria included *Bacteroides uniformis* (JCM5828), *Alistipes putredinis* (JCM16772), *Parabacteroides merdae* (JCM9497), *Bacteroides thetaiotaomicron* (JCM5827), *Lactococcus lactis* (JCM5805), and *Bifidobacterium breve* (JCM1192).

First, one day before co-culture, DMEM (high Glc; 10% FBS+P/S) of monolayered Caco-2 cells which had normally been cultured, was replaced with the same medium without antibiotics.

One day before co-culture, each bacterium was pre-cultured under anaerobic conditions at 37° C. for 12 hours using a GAM liquid medium (Nippon Suisan Kaisha, Ltd., Japan).

In the culture system I-GOEMON, an embodiment of the present disclosure, the liquid culture medium in the culture tank was a DMEM (high Glc) medium (10% FBS). The cell culture insert was placed in the system after culturing the monolayered Caco-2 cells in the cell culture insert.

The precultured liquid medium of anaerobic bacterial (OD600=2.0 (about $10^9$ cells/ml)) was diluted up to about $10^2$ cells/ml with anaerobic DMEM (high Glc) medium (10% FBS).

Five hundred µl of the diluted bacterial liquid culture medium was added into cell culture insert in the I-GOEMON culture system, and cultured in an anaerobic chamber with 0% $O_2$, 85% $N_2$, 5% $H_2$, 10% $CO_2$ anaerobic conditions for 2 days at 37° C. In addition, as a control, bacteria were also cultured in normal plastic wells.

The bacterial liquid culture medium was then collected. TER was measured for the monolayered Caco-2 cells in the cell culture insert of the culture system I-GOEMON.

The liquid culture medium was $10^0$-, $10^2$-, and $10^4$-fold diluted with the GAM medium, 100 µl of each diluted medium was inoculated onto GAM agar plate, cultured at 37° C. under anaerobic conditions, and the colony-forming unit (CFU) was calculated for each bacterium.

In addition, 16S rDNA was amplified by PCR from some colonies, and it was confirmed by sequence analysis that there was no contamination.

The results demonstrate that I-GOEMON facilitated significant growth promotion of a plurality of enteric bacteria species including uncultivable *Bacteroides* eubacteria (*Alistipes putredinis*), which are usually difficult to be proliferated under conventional culture conditions (FIG. 21). In addition, it was found that even if these enteric bacteria were present, the barrier function of Caco-2 cells was maintained in good condition for at least 2 days.

Surprisingly, despite the fact that the cultural condition was not optimized in the above tests, all of a plurality of enteric bacteria including *Bacteroides* eubacteria, which are difficult to be proliferated under conventional culture conditions, were found to have grown very efficiently thorough simple manipulation of static culture under anaerobic culture conditions using the culture system I-GOEMON as an embodiment of the present disclosure.

Experimental Example 5

Research for a Second Liquid Culture Medium Used in Cell Culture Insert for Isolation of Uncultured and Uncultivable Enteric Bacteria In the above tests, DMEM (high Glc; 10% FBS) was used as the second liquid culture medium. However, it was not confirmed whether said liquid culture medium had the optimum composition. Therefore, DMEM (high Glc), DMEM (no Glc) (10% FBS), DMEM (no Glc), and PBS were examined to find a composition of the liquid culture medium preferable for maintenance of intestinal epithelial cells cultured in the cell culture insert, in addition to said liquid culture medium.

1. Procedure

One day before the test, the DMEM (high Glc) medium (10% FBS+P/S) of the monolayered Caco-2 cells which had normally been cultured was replaced with the same medium without antibiotics.

One day before the test, DMEM (high Glc) (10% FBS), DMEM (high Glc), DMEM (no Glc) (10% FBS), DMEM (no Glc), and PBS were maintained in the anaerobic state. These medium were prepared for examination with the culture system of I-GOEMON according to an embodiment of the present disclosure.

On the day of the test start, DMEM (high Glc; 10% FBS) was injected into I-GOEMON's culture tank, and the cell culture insert was set to the system. Then, 500 µl (anaerobically treated) of each of DMEM (high Glc; 10% FBS), DMEM (high Glc), DMEM (no Glc; 10% FBS), DMEM (no Glc), and PBS was added to each cell culture insert.

The culturing was performed at 37° C. for 2 days in the anaerobic chamber with anaerobic environment of 0% $O_2$, 85% $N_2$, 5% $H_2$, and 10% $CO_2$, and then TER and extracellular LDH were measured.

2. Results

In the conventional anaerobic culture method with DMEM (high Glc; 10% FBS) as the second liquid culture medium, it was found impossible to maintain the intestinal epithelial cells in a good state until Day 5, which is an average renewal period of intestinal epithelial cells (FIGS. 22 and 23).

However, when the culture system of I-GOEMON was used, which is an embodiment of the present disclosure; it was found that the intestinal epithelial cells and the layer thereof were both maintained in a good state even when DMEM (high Glc) (10% FBS) was used. It was also found that the intestinal epithelial cells and the layers thereof were maintained in a good state in the same manner even in the liquid culture medium of DMEM (high Glc), DMEM (no Glc) (10% FBS), or DMEM (no Glc) having different compositions (FIGS. 22 and 23).

Surprisingly, I-GOEMON, an embodiment of the present disclosure was demonstrated to work even when an inorganic salt buffer solution (e.g. PBS) was used as a second liquid culture medium in the cell culture insert (FIGS. 22 and 23).

As suggested in the above results, the culture system placed in the anaerobic chamber was demonstrated to allow for maintenance of the epithelial cells and the layer thereof in preferable state, even with inorganic salt buffer as second culture medium. Therefore, the culture system and the culture method of the present disclosure for co-culturing of a bacterium (e.g. an anaerobic bacterium) with epithelial cells was demonstrated to be an outstanding culture system or culture method that may contribute to identifications of factors essential or inhibitory to culturing, and elucidation of mechanisms underlying them.

Experimental Example 6

Co-Culture Experiments for Isolation of Uncultured and Uncultivable Enteric Bacteria.
1. Preparation of Feces Stock After receiving approval from the university ethics committee, feces were donated from healthy volunteer. The collected feces were anaerobically stored under refrigeration and suspended in anaerobic 20% glycerol within several hours of collection. The suspended feces were aliquoted and stored under cryogenic conditions at −80° C.

The feces suspended in anaerobic 20% glycerol were cultured on GAM plates for 2 days. As a result, it was confirmed that the number of bacteria of about 1 to $15 \times 10^{11}$ CFU was included.
2. Co-Culture Caco-2 cells were inoculated into the cell culture insert of the culture system (I-GOEMON), which is an embodiment of the present disclosure, thereby forming the monolayered Caco-2 cells. One day before the test, the DMEM (high Glc) medium (10% FBS+P/S) in the cell culture insert was replaced with the same medium without antibiotics.

One day before co-culture, DMEM (high Glc) medium (10% FBS) was placed in an anaerobic chamber with an anaerobic environment of 0% $O_2$, 85% $N_2$, 5% $H_2$, and 10% $CO_2$ to make the liquid culture medium an anaerobic state.

Co-culture was started. To the culture tank of the culture system (I-GOEMON) as an embodiment of the present disclosure, DMEM (high Glc) medium (10% FBS) was injected, and the cell culture insert was set. As a control, DMEM (high Glc) medium (10% FBS) was injected into conventional culture petri dishes.

The feces stock was diluted $1/10^6$ in DMEM (high Glc) medium (10% FBS) used in the cell culture insert, 500 µl of the diluted feces sample was added to the set cell culture insert and the culture petri dish of the control, respectively, placed in the anaerobic chamber, and cultured for one day at 37° C. In addition, instead of DMEM (high Glc) (10% FBS), 500 µl of each of DMEM (high Glc), DMEM (no Glc) (10% FBS), DMEM (no Glc), DMEM (no Glc)+0.5% porcine stomach mucin and PBS (after anaerobic treatment) was added to each cell culture insert in the same manner as above, placed in the anaerobic chamber, and cultured at 37° C. for 1 day.

The test media in the cell culture insert of the culture system (I-GOEMON) as an embodiment of the present disclosure, and in the culture petri dishes of the control were suspended and collected.

The collected media were diluted $1/10^3$, and added to a newly set cell culture insert of the culture system (I-GOEMON) as an embodiment of the present disclosure, and to a culture petri dish of the control, and subcultured at 37° C. for 1 day.

The transepithelial electrical resistance value of the Caco-2 cell layer in the cell culture insert of the culture system (I-GOEMON) as an embodiment of the present disclosure, was measured.

Further, bacteria cultured in the cell culture insert of the culture system (I-GOEMON), which is an embodiment of the present disclosure, were collected together with Caco-2 cells. Bacteria cultured in the culture petri dish of the control were also collected.
3. Analysis of 16S rDNA Amplification and Flora Analysis Bacteria harvested together with Caco-2 cells cultured in the cell culture insert of the culture system (I-GOEMON), which is an embodiment of the present disclosure, and bacteria cultured in a control culture petri dish were subjected to bead milling, followed by phenol/chloroform extraction and further ethanol precipitation to extract the genome. Then, PCR using primers for 16S rDNA, i.e. U16SRT-F and U16SRT-R (Clifford R J et al., PLoS One 7: e48558 (2012) C3-C4 region) was performed to check whether or not 16S rDNA was amplified.

Figure 24:
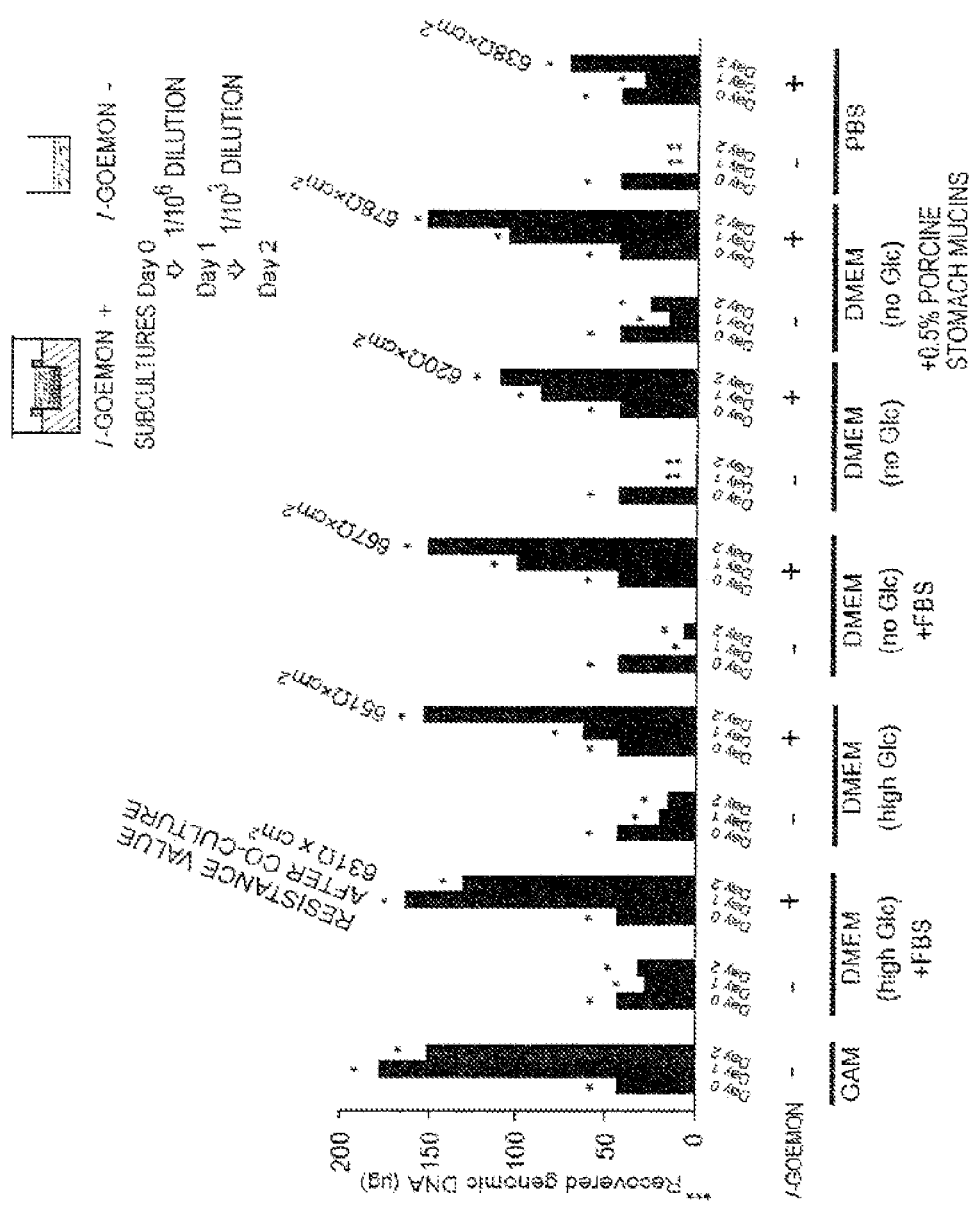
FIG. 24 depicts a graph showing resultant degrees of proliferation of anaerobic enteric bacteria collected from feces, in culture conducted in the culture system (I-GOEMON) as an embodiment of the present disclosure, for co-culturing of a bacterium (e.g. an anaerobic bacterium) with epithelial cells; as well as transepithelial electric resistance (TER) measurement for studying states of layers of intestinal epithelial cells after co-culturing. They were conducted for the purpose of isolation of uncultured and uncultivable enteric bacteria.

Further, bacteria harvested together with Caco-2 cells cultured in the cell culture insert of the culture system (I-GOEMON) which is an embodiment of the present disclosure were subjected to bacterial flora analysis.
4. Results As shown in FIG. 24, the culture system I-GOEMON as an embodiment of the present disclosure, was demonstrated to promote proliferation of fecal bacteria even in any case. Further, bacterial proliferation was observed even with PBS used in the upper portion. In addition, the barrier function of Caco-2 cells was also good. In addition, the proliferation of bacteria was found to correlate with the degree of increase in 16S rDNA copy number, showing the bacteria definitely proliferated.

Further, as shown in FIG. 24, addition of 0.5% porcine stomach mucin to the liquid culture medium of DMEM (no Glc) was found to allow for improvements in both of proliferation of the bacteria and maintenance of the barrier function of intestinal epithelial cells. The culture system I-GOEMON as an embodiment of the present disclosure was demonstrated to facilitate searches for factors involved in better culture of bacteria and maintenance of the barrier function of epithelial cells coexisting with the bacteria; and to provide effective measures for elucidation of mechanism in symbiotic relationship between bacterial flora in living beings and epithelial cells.

Experimental Example 7

Co-Culture Test (1) of Uncultivated Enteric Bacteria

The enteric bacterium, *Faecalibacterium prausnitzii* is a useful intestinal bacterium that has been reported to inhabit a digestive tract of humans, animals, poultry, and the like; and to have anti-inflammatory effects. In addition, this bacterium is extremely oxygen-sensitive, and requires anaerobic state for growth. However, it has been reported that even when co-cultured with epithelial cells under anaerobic state, it is impossible to proliferate the bacteria (Cellular Microbiology (2015), 17 (2), 226-240).

Meanwhile, as shown in the above-described respective Experimental Examples, the culture system I-GOEMON which is the measure and an embodiment of the present disclosure can achieve very efficient proliferation of enteric bacteria grown under anaerobic conditions of intestines.

Therefore, by using the culture system, I-GOEMON, which is an embodiment of the present disclosure, a test was conducted to confirm whether the proliferation of *Faecalibacterium prausnitzii*, which was conventionally difficult to achieve, can also be achieved.

1. Procurement of Bacteria

The intestinal bacterium, *Faecalibacterium prausnitzii* DSM 17677 (JCM31915), was obtained from National Research and Development Agency "RIKEN", the Institute of Physical and Chemical Research, Bio Resource Center (Tsukuba, Japan).

2. Co-Culture

Caco-2 cells were inoculated into the cell culture insert of the culture system (I-GOEMON), which is an embodiment of the present disclosure, thereby totaling the monolayered Caco-2 cells so as to cover the membrane of the cell culture insert. One day before the test, the DMEM (high Glc; 10% FBS+P/S) in the cell culture insert was replaced with the same medium without antibiotics.

One day before co-culture, DMEM (high Glc; 10% FBS) was placed in an anaerobic chamber with an anaerobic environment of 0% $O_2$, 85% $N_2$, 5% $H_2$, and 10% $CO_2$ to use the liquid culture medium under anaerobic conditions.

To the culture tank of the culture system (I-GOEMON), which is an embodiment of the present disclosure, DMEM (high Glc; 10% FBS) was injected, and the cell culture insert was set.

Further, one day before co-culture, pre-culture of *Faecalibacterium prausnitzii* was started under anaerobic conditions at 37° C. for 12 hours using Medium 1130 liquid medium (1130 YCFA MEDIUM) which is a medium for *Faecalibacterium prausnitzii*.

A co-culture test was then started. The pre-cultured *Faecalibacterium prausnitzii* was diluted in a liquid medium, GAM (Nippon Suisan Kaisha, Ltd., Japan) or Medium 1130, the bacterial cells were added to the cell culture insert (+cell conditions) where the Caco-2 cells were inoculate in the culture system (I-GOEMON) which is an embodiment of the present disclosure, and cultured under the anaerobic conditions at 37° C. for 12 hours in the anaerobic chamber, and the Caco-2 cells and bacteria were collected. In addition, the diluted *Faecalibacterium prausnitzii* was added to GAM, a liquid medium, and Medium 1130 liquid medium to form controls (−cell conditions).

3. Confirmation and Analysis of 16S rDNA Amplification

*Faecalibacterium prausnitzii* cells were harvested together with Caco-2 cells cultured in the cell culture insert of the culture system (I-GOEMON), which is an embodiment of the present disclosure. As a control, *Faecalibacterium prausnitzii* was cultured and then in order to make the extraction conditions equal, Caco-2 cells were added thereto. Both were individually subjected to bead milling, addition of pUC19 plasmid as an internal standard, followed by phenol/chloroform extraction and further ethanol precipitation to extract the genome. Then, PCR using primers for 16S rDNA (U16SRT-F and U16SRT-R (Clifford R J et al., PLoS One 7: e48558 (2012) C3-C4 region)), and PCR using a primer set for detecting pUC19 plasmid were performed to quantify the copy numbers of 16S rDNA and pUC19 plasmid, respectively. Then, the copy number of total 16S rDNA was calculated, corrected using pUC19 recovery rate, and then compared.

4. Results

As shown in FIG. 25, the culture system I-GOEMON as an embodiment of the present disclosure was used to co-culture *Faecalibacterium prausnitzii* in a medium for *Faecalibacterium prausnitzii* (Medium 1130 liquid medium) under anaerobic conditions with Caco-2 cells inoculated on and monolayered so as to cover the membrane of the cell culture insert (+cell condition). This proliferation of *Faecalibacterium prausnitzii* was found to be remarkable as compared to that in the conventional culture method with M1130 liquid medium in absence of Caco-2 cells (−cell condition).

Further, the system had received *Faecalibacterium prausnitzii* diluted in a general-purpose liquid medium GAM with Caco-2 cells inoculated on and monolayered so as to cover the membrane of the cell culture insert (+cell condition), allowing for the proliferation of the bacterium. This proliferation of *Faecalibacterium prausnitzii* was found to be remarkable compared to that in absence of Caco-2 cells (−cell condition), as indicated in FIG. 25. Optimization of culture conditions is formidable, especially in culturing unidentified or small number of bacteria. However, I-GOEMON as an embodiment of the present disclosure was demonstrated to allow for proliferating bacteria without such optimization of culture conditions for them in advance before culturing them in a general-purpose liquid medium GAM. This was considered to be remarkable effects.

The measure of the present disclosure has been demonstrated to allow its users to more effectively proliferate a subject identified bacterium than conventional measures during further exploration of the bacterium. Further, the current measure has also been demonstrated to contribute to effective proliferation of a subject bacterium unidentified or obtained in trace amounts; and elucidation of the underlying mechanism of symbiotic relationship between the subject bacteria and epithelial cells.

Experimental Example 8

Co-Culture Test (2) of Enteric Bacteria of which Culture and Proliferation are Difficult It was reported to be difficult to proliferate *Faecalibacterium prausnitzii*, an intestinal bacterium even when co-cultured with epithelial cells in an anaerobic condition; and that *Faecalibacterium prausnitzii* was dead during the co-culture (Cellular Microbiology (2015), 17 (2), 226-240).

Meanwhile, as shown in Experimental Example 7, the culture system (I-GOEMON) as an embodiment of the present disclosure was demonstrated to allow for remarkable proliferation of *Faecalibacterium prausnitzii*, as compared to the conventional methods although the bacterium was known to be difficult to culture. Then, coculture experiment was conducted to further demonstrate that the measure of the present disclosure I-GOEMON was remarkably effective in co-cultured cells-mediated prolonged proliferation of *Faecalibacterium prausnitzii* without liquid culture media individually optimized for the subject bacteria. Specifically, the experiment of coculture of *Faecalibacterium prausnitzii* with Caco-2 cells was conducted with I-GOEMON and a culture medium made for Caco-2 cells, not for *Faecalibacterium prausnitzii*.

1. Preparation of Bacteria.

As in Experimental Example 8, *Faecalibacterium prausnitzii* DSM 17677 (JCM31915), an enteric bacterium, was used.

2. Co-Culture

Caco-2 cells were inoculated into the cell culture insert of the culture system (I-GOEMON) as an embodiment of the present disclosure, thereby having the Caco-2 cells monolayered so as to cover the membrane of the cell culture insert. One day before the test, the DMEM (high Glc)

medium (10% FBS+P/S) in the cell culture insert was replaced with the same medium without antibiotics.

One day before co-culture, DMEM (high. Glc; 10% FBS) was placed in an anaerobic chamber with an anaerobic environment of 0% $O_2$, 85% $N_2$, 5% $H_2$, and 10% $CO_2$ to use the liquid culture medium under anaerobic conditions.

To the culture tank of the culture system (I-GOEMON), which is an embodiment of the present disclosure, DMEM (high Glc; 10% FBS) was injected, and the cell culture insert was set.

Further, one day before co-culture, pre-culture of *Faecalibacterium prausnitzii* was started under anaerobic conditions at 37° C. for 12 hours using Medium 1130 liquid medium (1130 YCFA MEDIUM) which is a medium for *Faecalibacterium prausnitzii*.

A co-culture test was then started. The pre-cultured *Faecalibacterium prausnitzii* was diluted with DMEM (high Glc) without FBS and antibiotics; added to the cell culture insert with the inoculated Caco-2 cells, of the culture system (I-GOEMON), which is an embodiment of the present disclosure; and cultured in an anaerobic chamber at 37° C. under anaerobic conditions. Caco-2 cells and bacteria were collected immediately after the culture started, and then at 8 and 48 hours after it started.

3. Confirmation and Analysis of 16S rDNA Amplification

*Faecalibacterium prausnitzii* collected together with Caco-2 cells was subjected to bead milling, followed by addition of pUC19 plasmid as an internal standard, phenol/chloroform extraction and ethanol precipitation, to extract the genome. Then, PCR assays were conducted using primers for 16S rDNA, i.e. U16SRT-F and U16SRT-R (Clifford R J et al., PLoS One 7: e48558 (2012) C3-C4 region) and primer sets for detecting pUC19 plasmid, to quantify copy numbers of 16S rDNA and pUC19 plasmid, respectively. Then, the copy number of total 16S rDNA was calculated, corrected using pUC19 recovery rate, and then compared.

4. Results

As shown in FIG. 26, the culture system, I-GOEMON, which is an embodiment of the present disclosure, remarkably enhanced proliferation of *Faecalibacterium prausnitzii* when observed at 8 hours after the co-culture was started. Further, the system also remarkably enhanced proliferation of *Faecalibacterium prausnitzii* when observed at 48 hours after the co-culture was started. Those demonstrated that the measure of the present disclosure was remarkably effective in co-cultured cells-mediated prolonged continuous proliferation of *Faecalibacterium prausnitzii*. These test results are surprising in view of the report that intestinal bacterium *Faecalibacterium prausnitzii* had been killed during co-culture with epithelial cells in anaerobic condition (Cellular Microbiology (2015), 17 (2), 226-240). Therefore, the current results support very high usefulness of the present disclosure.

Experimental Example 9

Influence of Cell Layers in Cell Culture Inserts on Dissolved Oxygen Concentration As validated in Experimental Example 1, just placing the culture system of the present disclosure in the anaerobic chamber has allowed for five-day maintenance of anaerobic and aerobic environments in the cell culture insert and in the culture tank, respectively. In this regard, the anaerobic and aerobic environments was established to reflect actual environments of intestinal lumen in the intestinal tract, and the blood vessel side of the intestinal epithelial cell layer, respectively. This implies that the structure of the culture system of the present disclosure has achieved maintenance of lower and higher concentrations of dissolved oxygen in the upper and lower tanks, i.e. the spaces above and below the cell layer, respectively. To further validate the above features, we have demonstrated that removal of the cell layers of Caco-2 cells from the culture system of the present disclosure lead to disruption in aerobic environment of the culture tank. As stated above, the aerobic environment in the tank was intended to reflect actual environment in the blood vessel side of the intestinal epithelial cell layer.

This experimental example was performed in the same manner as in Example 1 except that the cell culture insert was mounted without inoculating Caco-2 cells, and that the cell culture insert was not mounted. In this example, the culture system (I-GOEMON) as an embodiment of the present disclosure, was also maintained in the anaerobic chamber with an anaerobic environment of 0% $O_2$, 85% $N_2$, 5% $H_2$, and 10% $CO_2$. Then, oxygen concentration of the liquid culture medium in the culture tank and the cell culture insert was measured using a non-destructive needle type oxygen transmitter Microx TX3 (Micro fiber optic oxygen transmitter, PreSens).

As described in Experimental Example 1, when Caco-2 cells were inoculated to cover the cell culture insert in the culture system (I-GOEMON), which is an embodiment of the present disclosure, dissolved oxygen concentrations in the tank under the cell culture insert were maintained at high level (FIG. 14).

Meanwhile, Experimental Example 9 demonstrated that when no cell culture insert was mounted, oxygen saturation of the solution in the culture tank decreased to about 20% after 2 hours from starting the test, and to 0% after 6 hours. The Example also demonstrated that when the cell culture insert was mounted without inoculating Caco-2 cells, oxygen saturation of the solution in the culture tank, i.e., under the cell culture insert, was consistently decreased and became almost 0% at 12 hours (FIG. 27).

In addition, as described in Experimental Example 1, when Caco-2 cells were inoculated to cover the cell culture insert in the culture system (I-GOEMON), which is an embodiment of the present disclosure, the dissolved oxygen concentration in the upper space above the cell culture insert was maintained at lower level as less than 1% (FIG. 14).

Meanwhile, Experimental Example 9 demonstrated that when a cell culture insert was mounted without inoculating Caco-2 cells, oxygen saturation of the solution in the upper space above the cell culture insert, that is, in the inside of the cell culture insert increased up to about 10% temporarily (FIG. 27).

The culture system of the present disclosure was demonstrated to allow for preferable proliferation of uncultivable enteric bacteria. This implies that the inoculated Caco-2 cell layer contributed to prolonged maintenance of higher and lower levels of oxygen saturation in the culture tank and the cell culture insert, respectively.

Experimental Example 10

With Respect to Effect of Gas Impermeable Sealing Agent Sealing the Cell Culture Insert and the Opening of the Culture Tank on Dissolved Oxygen Concentration Further, in the culture system of the present disclosure, a test was performed to confirm the influence of the gas-impermeable sealing agent sealing the cell culture insert and the opening of the culture tank on dissolved oxygen concentration.

Experimental Example 10 was performed in the same manner as in Example 1 except that the gas-impermeable sealing agent for sealing the cell culture insert and the opening of the culture tank was not attached in the culture system (I-GOEMON) which is an embodiment of the present disclosure, and the culture system was placed to stand in the anaerobic chamber with anaerobic environment of 0% $O_2$, 85% $N_2$, 5% $H_2$, and 10% $CO_2$. Then, oxygen concentrations of liquid culture media in the culture tank and the cell culture insert were measured using a non-destructive needle type oxygen transmitter Microx TX3 (Micro fiber optic oxygen transmitter, PreSens).

According to Experimental Example 1, when using the gas-impermeable sealing agent for sealing the cell culture insert and the opening of the culture tank in the culture system (I-GOEMON) as an embodiment of the present disclosure, high dissolved oxygen concentration was maintained for 5 days in the culture tank, i.e., under the cell culture insert (FIG. 14).

Meanwhile, it was found that without the gas-impermeable sealing agent for sealing the cell culture insert and the opening of the culture tank in Experimental Example 10, the dissolved oxygen concentration in the cell culture insert, i.e., in the upper part (inside) of the cell culture insert, was almost 0%, but the dissolved oxygen concentration in the culture tank, i.e., under the cell culture insert, was consistently decreased, specifically, decreased to 60%, 10%, and almost 0% at elapsed time of 24, 36, and 48 hours, respectively (FIG. 28).

In the culture system of the present disclosure, which is confirmed to be capable of satisfactorily performing proliferation of uncultivable enteric bacteria the gas-impermeable sealing agent for sealing the openings of the cell culture insert and the culture tank continuously maintained oxygen saturation of the culture tank, i.e., the space under the cell culture insert, to be high for prolonged period of time.

Experimental Example 11

By performing tests for evaluating the state of intestinal epithelial cells when cultured using I-GOEMON, which is an embodiment of the present disclosure, it was confirmed that the barrier function of tight junctions of monolayered Caco-2 cells for 5 days was maintained to be a good state to the same extent as that of culture under the aerobic condition environment at the time of Caco-2 culture, in transepithelial electric resistance (TER) measurement, extracellular lactate dehydrogenase (LDH) activity measurement, and intracellular LDH activity measurement in Experimental Example 2.

Thus, in Experimental Example 11, a test using immunohistological staining was also performed to confirm that the barrier function due to the tight junction of the monolayered Caco-2 cells was well-maintained for 5 days.

Reagents were prepared as follows: PBS-MC (PBS including 1 mM $MgCl_2$. 0.1 mM $CaCl_2$), Blocking One (NACALAI TESQUE, INC., Japan), antibody diluent [PBS-MC: Blocking One=1:3], ProLong anti-fading sealant (anti-fade) (Thermo Fisher), and DAPI (Invitrogen-Thermo Fisher Scientific). Further, antibodies were prepared as follows: anti-Claudin 2 antibody (Life Technologies-Thermo Fisher Scientific) diluted 1/125, anti-rabbit IgG (goat) (Alexa 488) (Molecular Probe-Thermo Fisher Scientific) diluted 1/1000, and anti-goat IgG (rabbit) (Alexa 488) (Molecular Probe-Thermo Fisher Scientific) diluted 1/500.

The same manner as that in Experimental Example 2 above applied to this Example. Specifically, the culture system (I-GOEMON) as an embodiment of the present disclosure, and the conventional culture systems were used under anaerobic conditions ("Anaero") and under aerobic conditions ("Aero"); and the cells were inoculated on the porous membrane in the cell culture insert to form the layer, and set in each culture tank. The I-GOEMON and the conventional culture system ("Anaero") for culturing were placed in an anaerobic chamber; and the conventional culture system ("Aero") for culturing was placed in a $CO_2$ incubator.

Monolayer-cultured Caco-2 cells were washed 3 times with PBS-MC. Cells were fixed with ice-cold methanol at −20° C. for 20 minutes. The cells were washed once with PBS-MC, and the membrane was cut and removed from the cell culture insert. Thereafter, the membrane was incubated at room temperature for 1 hour using Blocking One. It was then subjected to reactions overnight at 4° C. with the primary antibody (anti-Claudin 2 antibody) diluted with antibody diluent. Further, it was subjected to washing three times with PBS-MC followed by reactions at room temperature for one hour with the secondary antibody (anti-rabbit Alexa 488) diluted with antibody diluent. Then, it was subjected to washing three times with PBS-MC, followed by reactions at room temperature for one hour with the tertiary antibody (anti-goat Alexa 488) diluted with antibody diluent and 0.1 µg/ml DAPI. It was then subjected to washing three times with PBS-MC, followed by mounting process using ProLong anti fade mountant. Then, it was observed with confocal microscope (Nikon, A1Rsi). Results thereof are shown in FIG. 29.

Under the anaerobic condition ("Anaero") on Day 5, the conventional system was found to have their monolayered Caco-2 cells damaged; and the cells to lose tight junctions (FIG. 23). Meanwhile, even under anaerobic conditions, similar to the conventional conditions of the culture system ("Aero"), the culture system (I-GOEMON) was demonstrated to maintain the monolayered Caco-2 cells in a good state with tight junctions maintained between them in the whole during prolonged period of 5 days (FIG. 29).

REFERENCE SIGNS LIST 1 culture tank
1a opening
2 cell culture insert
3 porous membrane
4 gas-impermeable sealing agent
5 gas-permeable moisturizing members
6 epithelial cells
7 liquid culture medium in aerobic state
8 second liquid culture medium
10 cell such as anaerobic cell
11 nucleus
12 tight junctions

The invention claimed is:

1. A culture system for co-culturing a first cell group consisting of one or more kinds of cells and a cell layer or tissue formed of a second cell group consisting of one or more kinds of cells different from the former cells, the culture system comprising:
(i) at least one first culture tank for co-culturing, under an anaerobic condition, the first cell group and the cell layer or tissue formed of the second cell group;
(ii) a gas-permeable moisturizing member for sealing an opening of a space maintaining the anaerobic condition, wherein the gas-permeable moisturizing member allows oxygen which has flowed from the second culture tank through the permeable structure into the first culture tank to move toward the outside while preventing the inside of the first culture tank from being dried;

(iii) a second culture tank for pooling a liquid culture medium of an aerobic condition; and (iv) a permeable structure positioned between the first culture tank and the second culture tank, wherein (a) the permeable structure is permeable to liquid culture media and components dissolved therein, and (b) the permeable structure is impermeable to the cell layer or the tissue formed in the first culture tank.

2. The culture system according to claim 1, wherein an opening is closed between the second culture tank and the first culture tank so that an inside of the second culture tank is closed except for the permeable structure positioned between the first culture tank and the second culture tank; and a gas-impermeable sealing agent is provided at a connection part between the first culture tank and the second culture tank.

3. The culture system according to claim 1, wherein the first culture tank includes a plurality of sub-culture tanks therein, and each of the sub-culture tanks is individually interconnected by a permeable structure, and each of the plurality of sub-culture tanks is connected to the second culture tank.

4. The culture system according to claim 1, wherein the culture system is configured to be placed in an anaerobic chamber in use.

5. A culture system for co-culturing a bacterium with a cell layer formed of epithelial cells, the culture system comprising:

a first culture tank configured to be used under an anaerobic condition;

a second culture tank; and a gas-impermeable sealing agent;

wherein the first culture tank has one or more permeable structures in a bottom thereof so as to allow the cell layer to cover each top surface of the permeable structures;

wherein the second culture tank is a tank for pooling a liquid culture medium of an aerobic condition, and has an opening for receiving the first culture tank so that the permeable structure in the bottom of the first culture tank is immersed in the liquid culture medium of an aerobic condition pooled in the second culture tank;

wherein an opening is closed between the second culture tank and the first culture tank so that an inside of the second culture tank is closed except for the permeable structure wherein a gas-impermeable sealing agent is provided at a connection part between the first culture tank and the second culture tank;

wherein the second culture tank comprises a gas-permeable moisturizing member for sealing an opening thereon to the outside so that the second culture tank has no part therein opened to the outside with the opening sealed by the gas-permeable moisturizing member; and wherein the gas-permeable moisturizing member allows oxygen which has flowed from the second culture tank through the permeable structure into the first culture tank to move toward the outside while preventing the inside of the first culture tank from being dried.

* * * * *